United States Patent
Ohnishi et al.

(10) Patent No.: US 7,641,609 B2
(45) Date of Patent: Jan. 5, 2010

(54) ENDOSCOPE DEVICE AND NAVIGATION METHOD FOR ENDOSCOPE DEVICE

(75) Inventors: Junichi Ohnishi, Hachioji (JP); Shunya Akimoto, Hachioji (JP); Eiichi Kobayashi, Tama (JP); Fumihiro Asano, Gifu (JP); Hiroshi Moriya, Fukushima (JP)

(73) Assignee: Olympus Corporation, Tokyo (JP)

( * ) Notice: Subject to any disclaimer, the term of this patent is extended or adjusted under 35 U.S.C. 154(b) by 493 days.

(21) Appl. No.: 10/498,155

(22) PCT Filed: Jul. 31, 2003

(86) PCT No.: PCT/JP03/09733
§ 371 (c)(1),
(2), (4) Date: Jun. 8, 2004

(87) PCT Pub. No.: WO2004/010857
PCT Pub. Date: Feb. 5, 2004

(65) Prior Publication Data
US 2005/0020878 A1    Jan. 27, 2005

(30) Foreign Application Priority Data
Jul. 31, 2002    (JP)    .............................. 2002-223618

(51) Int. Cl.
*A61B 1/00* (2006.01)
*A61B 1/04* (2006.01)

(52) U.S. Cl. ....................... 600/117; 600/145

(58) Field of Classification Search ................ 600/103, 600/114, 117, 118, 407
See application file for complete search history.

(56) References Cited

U.S. PATENT DOCUMENTS

| | | | | |
|---|---|---|---|---|
| 5,417,210 A | * | 5/1995 | Funda et al. ................. | 600/425 |
| 5,526,812 A | * | 6/1996 | Dumoulin et al. ........... | 600/407 |
| 5,765,561 A | * | 6/1998 | Chen et al. .................. | 600/407 |
| 5,873,822 A | * | 2/1999 | Ferre et al. .................. | 600/407 |
| 6,346,940 B1 | * | 2/2002 | Fukunaga .................... | 345/427 |
| 6,602,185 B1 | * | 8/2003 | Uchikubo .................... | 600/118 |
| 6,702,736 B2 | * | 3/2004 | Chen et al. .................. | 600/117 |
| 6,801,643 B2 | * | 10/2004 | Pieper ........................ | 382/128 |
| 2003/0184598 A1 | * | 10/2003 | Graham ....................... | 345/838 |
| 2004/0205504 A1 | * | 10/2004 | Phillips .................... | 715/501.1 |

FOREIGN PATENT DOCUMENTS

| | | |
|---|---|---|
| JP | 2000-135215 | 5/2000 |
| JP | 2002-200030 | 7/2002 |

* cited by examiner

*Primary Examiner*—John P Leubecker
*Assistant Examiner*—Philip R Smith
(74) *Attorney, Agent, or Firm*—Scully, Scott, Murphy & Presser, P.C.

(57) ABSTRACT

In an endoscope device 1 in accordance with the present invention, a navigation screen 51 is displayed. The navigation screen 51 includes: an endoscopic live image display area 52 in which a live image produced by a bronchoscope 2 is displayed; a VBS image display area 53 in which a VBS image is displayed; and a thumbnail VBS image area 54 in which images constructed by reducing VBS images that represent all branch points on a route are displayed as thumbnail VBS images representing branch points. Consequently, an endoscope can be reliably navigated to reach a target region using guide images that represent actual branch positions.

16 Claims, 31 Drawing Sheets

ENDOSCOPE DEVICE AND NAVIGATION METHOD FOR ENDOSCOPE DEVICE

TECHNICAL FIELD

The present invention relates to an endoscope device, or more particularly, an endoscope device capable of navigating an endoscope to help insert the endoscope into an intracorporeal lumen, for example, the bronchi.

BACKGROUND ART

In recent years, diagnosis based on images has been widely adopted. For example, an X-ray computed tomography (CT) device is used to produce tomographic images of a subject so as to construct three-dimensional image data representing the interior of the subject. The three-dimensional image data is used to diagnose a lesion.

As far as the CT system is concerned, while an X-ray irradiation and detection unit is continuously rotated, a subject is continuously moved in the direction of the body axis. Thus, helical scanning is performed on the three-dimensional field of the subject, and a three-dimensional image is produced based on tomographic images that represent successive sections of the subject in the three-dimensional field.

One of such three-dimensional images is a three-dimensional image representing the bronchi in the lungs. The three-dimensional image of the bronchi is utilized in order to three-dimensionally grasp the position of an abnormality that is suspected to be, for example, a pulmonary carcinoma. In order to check the abnormality through biopsy, a bronchoscope is inserted in order to collect a sample of a tissue using a biopsy needle located in the distal section of the endoscope.

FIG. 31 shows a bronchi 500. As far as an intracorporeal lumen that branches out in multiple stages is concerned, when the position of an abnormality is close to the terminal of a branch, it is hard to lead the distal end of an endoscope to a target region accurately for a short period of time. For example, Japanese Unexamined Patent Application Publication No. 2000-135215 has proposed a system for navigating a bronchoscope to a target region. Herein, a three-dimensional image of an intracorporeal lumen of a subject is constructed based on image data acquired from a three-dimensional field of the subject. The course to a target point along the lumen is determined using the three-dimensional image. Virtual endoscopic images representing regions of the lumen that lie along the course are constructed based on the image data, and displayed in order to navigate a bronchoscope.

However, the navigation to a target region to be performed in the system described in the Japanese Unexamined Patent Application Publication No. 2000-135215 includes display of a live endoscopic image produced by the bronchoscope. In addition, virtual endoscopic images representing branch points of bronchi are displayed for the purpose of guiding the bronchoscope into a destination of insertion. As mentioned above, the bronchi branch out in multiple stages. Moreover, images constructed with the bronchoscope located in the respective bronchi are images representing a plurality of branch destinations and resembling one another. When virtual endoscopic images are merely displayed, even if the virtual endoscopic images represent branch positions different from actual branch positions represented by a live endoscopic image, an operator may misidentify the virtual endoscopic images as images representing the correct branch positions. The misidentification may become a serious obstacle to navigation of the bronchoscope to a target region.

The present invention attempts to break through the foregoing situation. An object of the present invention is to provide an endoscope device capable of reliably navigating an endoscope to a target region using guide images that represent actual branch positions.

DISCLOSURE OF INVENTION

An endoscope device in accordance with the present invention comprises: three-dimensional image constructing means for constructing a three-dimensional image of an intracorporeal lumen of a subject on the basis of images representing a three-dimensional field of the subject; an endoscope that picks up images of the intracorporeal lumen of the subject; and navigation image constructing means that constructs a navigation image which includes the endoscopic image of the intracorporeal lumen of the subject that is produced by the endoscope and the three-dimensional image. While presenting the course of the endoscope to be steered in order to insert the endoscope into the intracorporeal lumen of the subject, the endoscope device helps observe or treat the subject. Herein, the navigation image constructing means constructs the navigation image adding reduced images of three-dimensional images, which represent all branch points at which the intracorporeal lumen of the subject branches out, added thereto. Owing to these constituent features, the endoscope can be reliably navigated to reach a target region using guide images representing the actual branch positions.

BEST MODE FOR CARRYING OUT THE INVENTION

Figure 1:
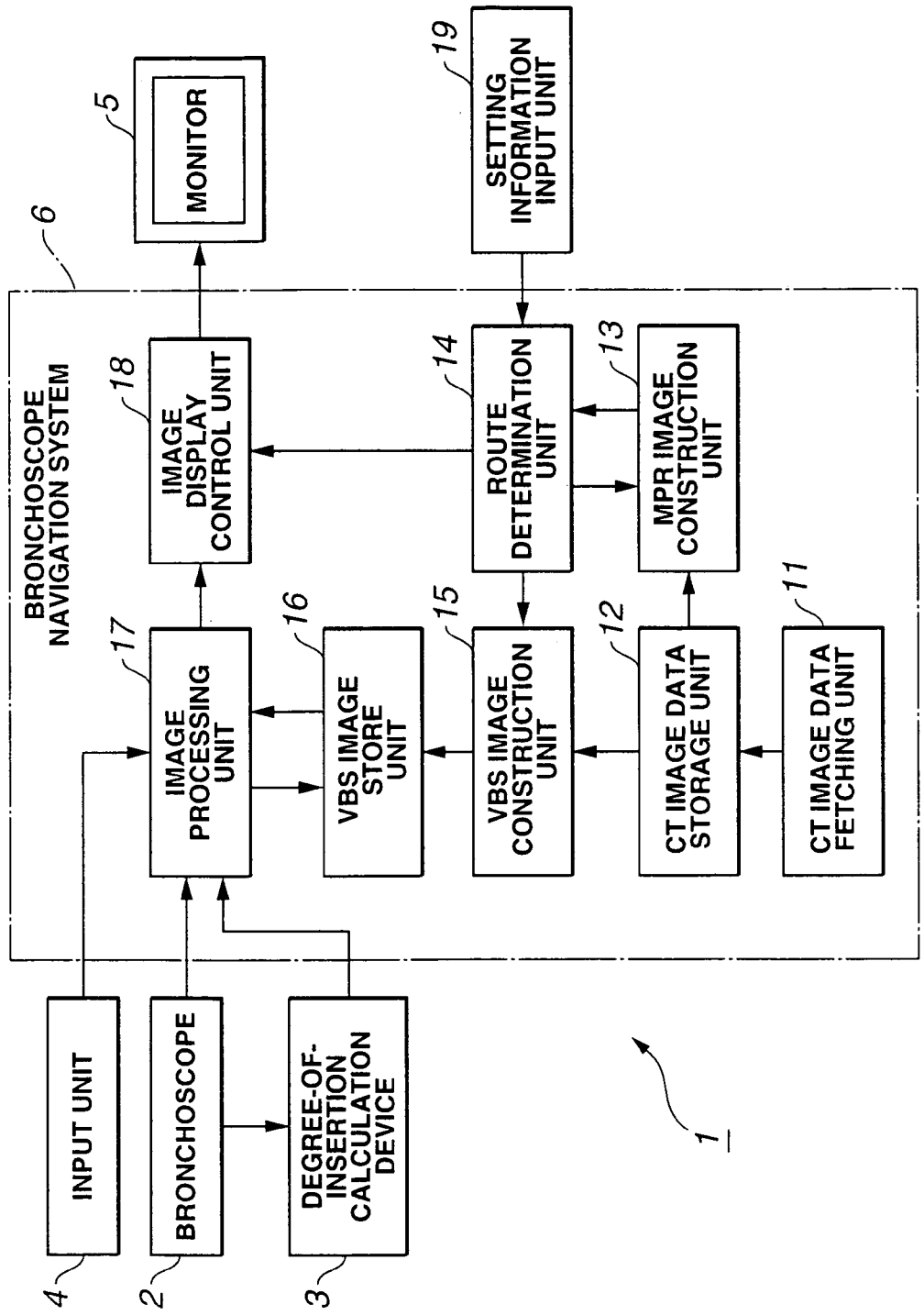
FIG. 1 shows the configuration of an endoscope device in accordance with an embodiment of the present invention.

Referring to the drawings, an embodiment of the present invention will be described below.

Figure 2:
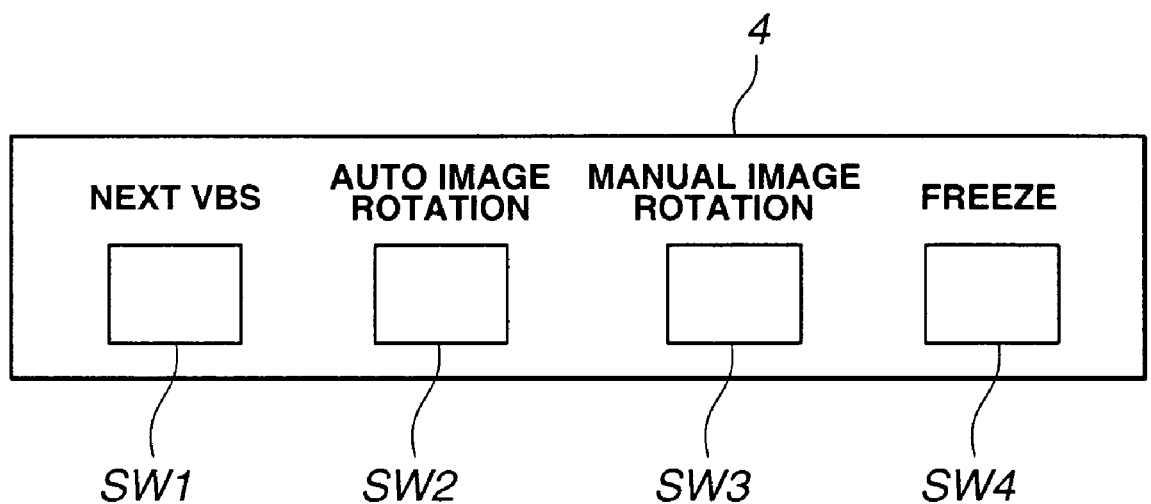
FIG. 2 shows the configuration of an input unit shown in FIG. 1.
Figure 3:
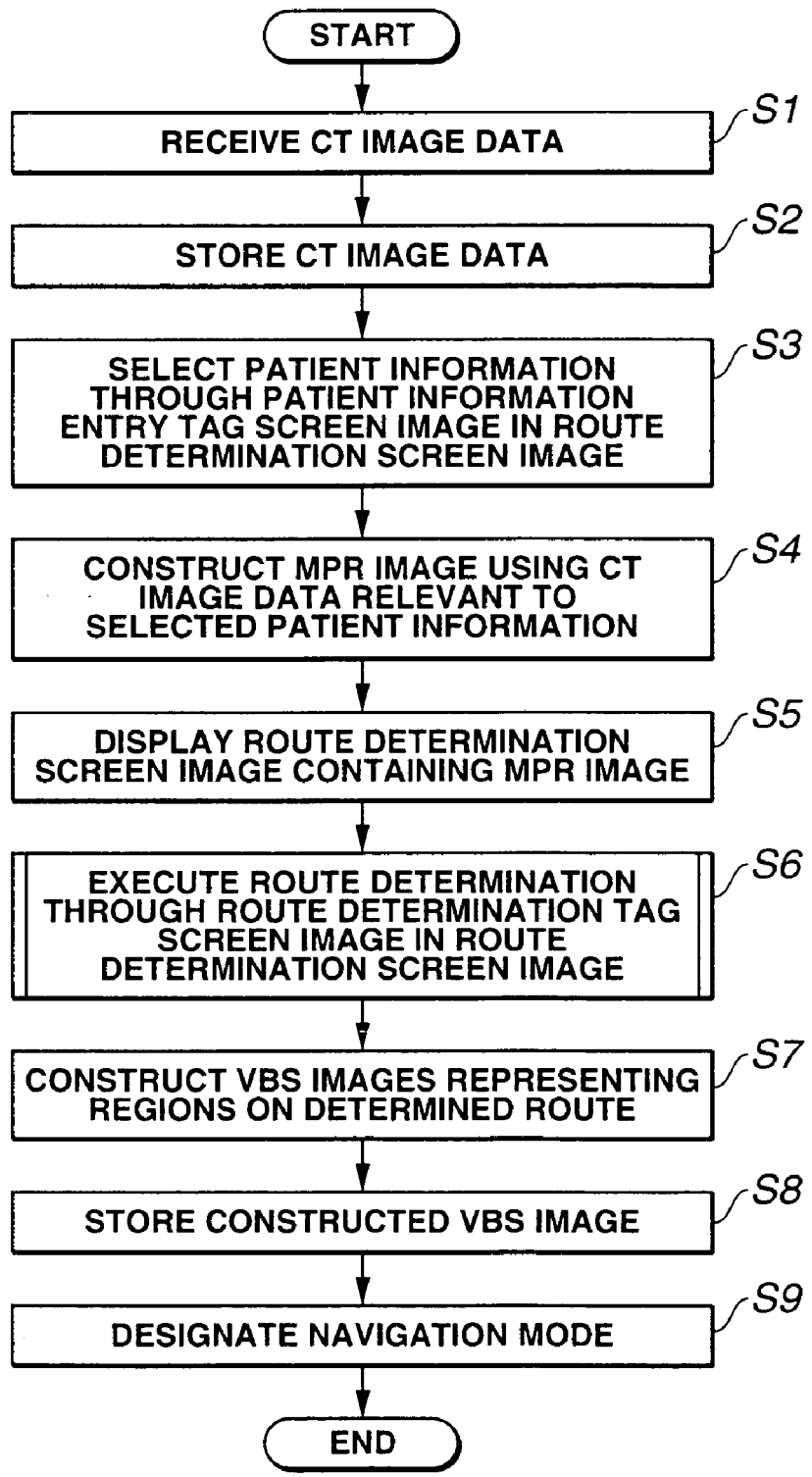
FIG. 3 is a flowchart describing the flow of constructing navigation data to be executed by a bronchoscope navigation device shown in FIG. 1.
Figure 4:
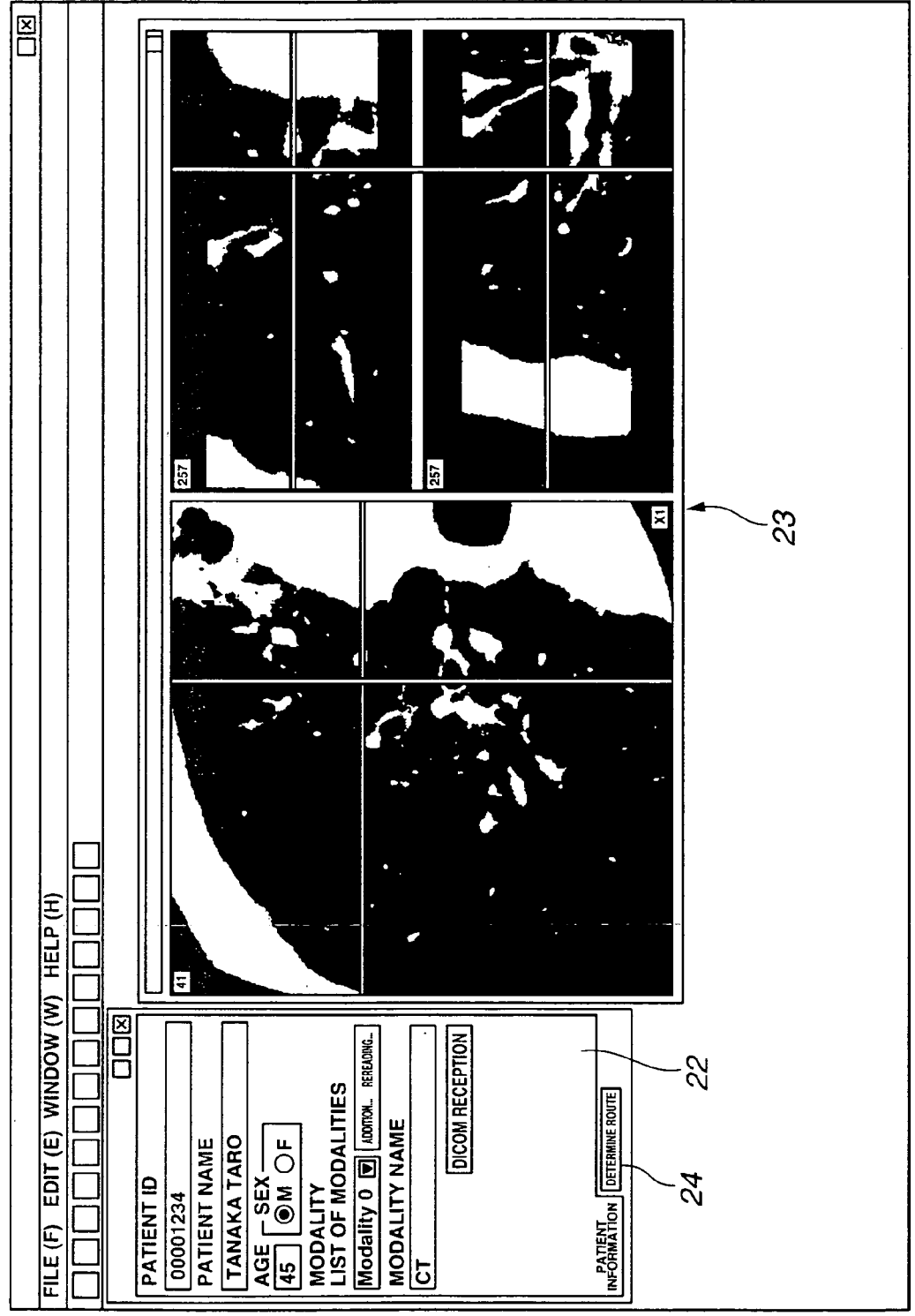
FIG. 4 is a first diagram showing a route determination screen in which the execution of the process described in FIG. 3 is performed.
Figure 5:
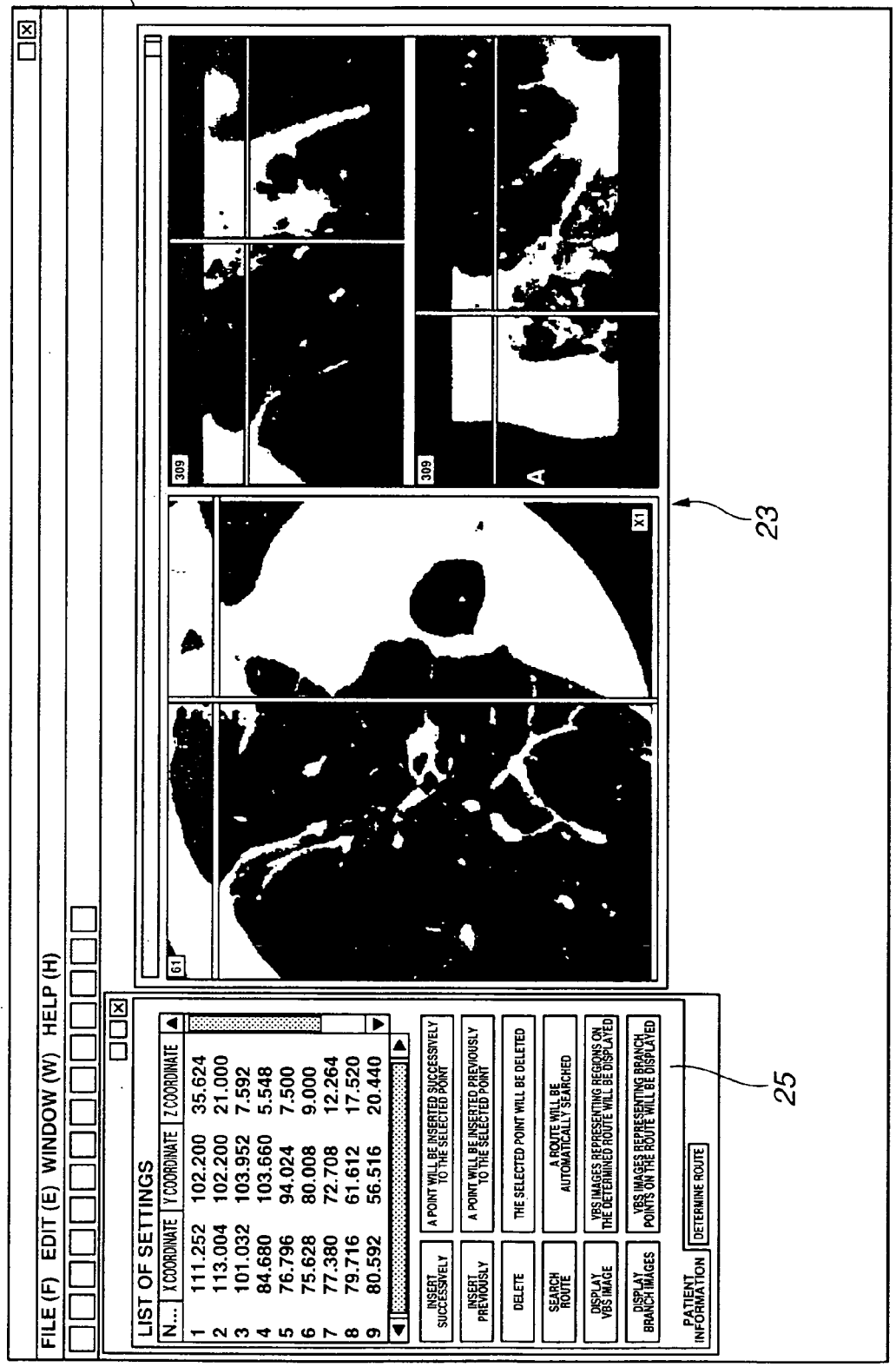
FIG. 5 is a second diagram showing the route determination screen in which the execution of the process described in FIG. 3 is performed.
Figure 6:
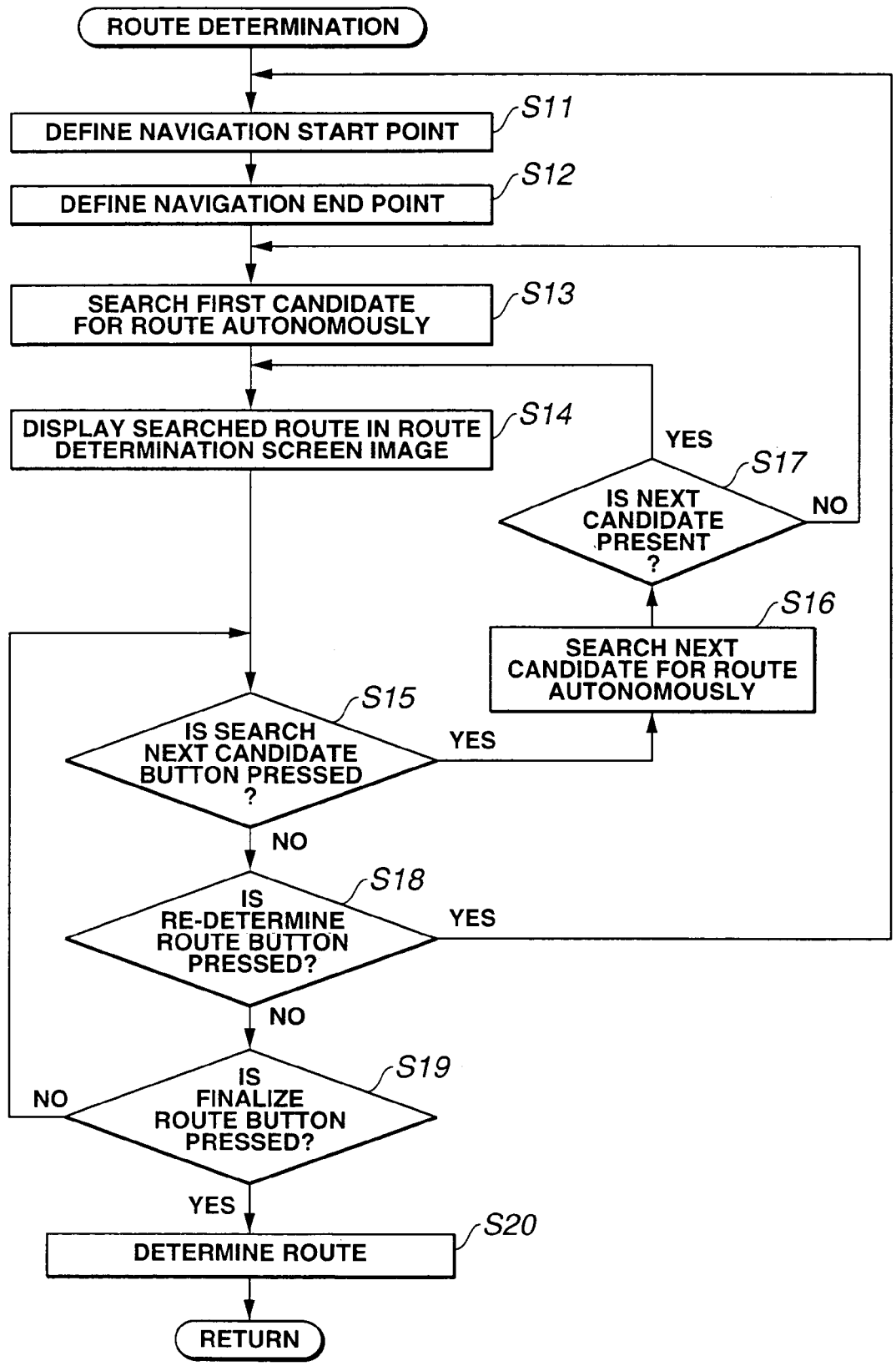
FIG. 6 is a flowchart describing the flow of determining a route.
Figure 7:
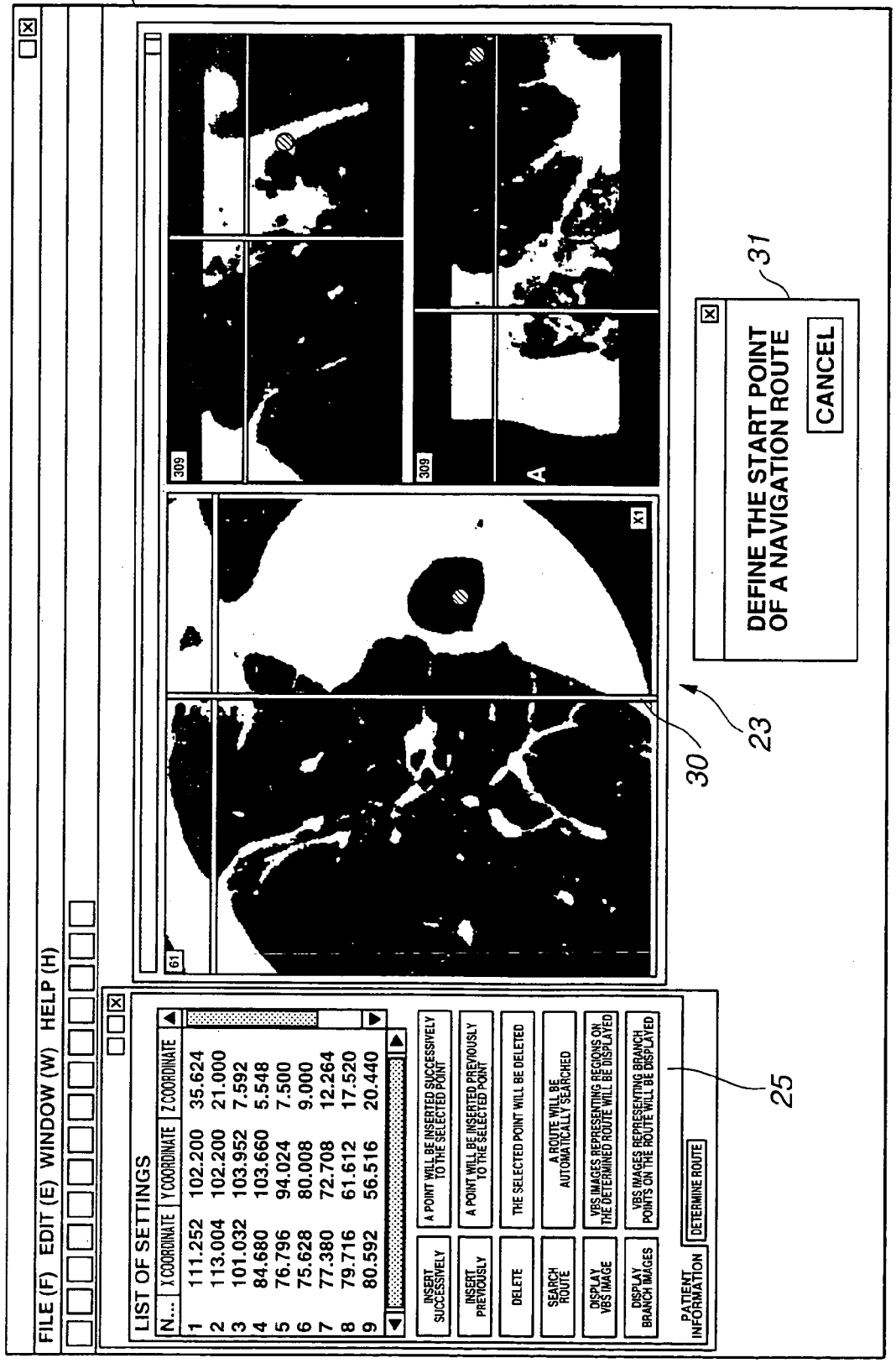
FIG. 7 is a first diagram showing a route determination screen in which the execution of the process described in FIG. 6 is performed.
Figure 8:
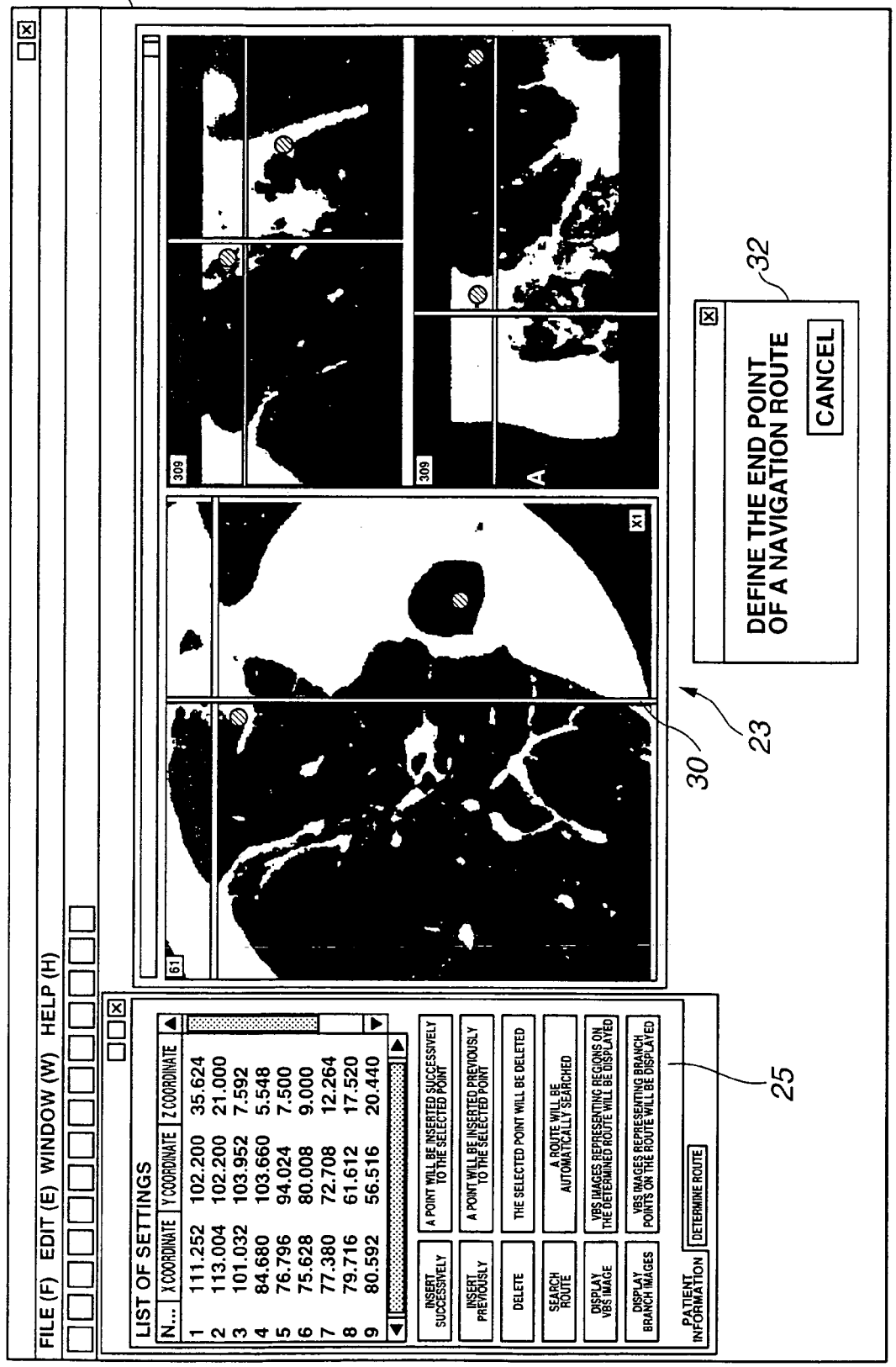
FIG. 8 is a second diagram showing the route determination screen in which the execution of the process described in FIG. 6 is performed.
Figure 9:
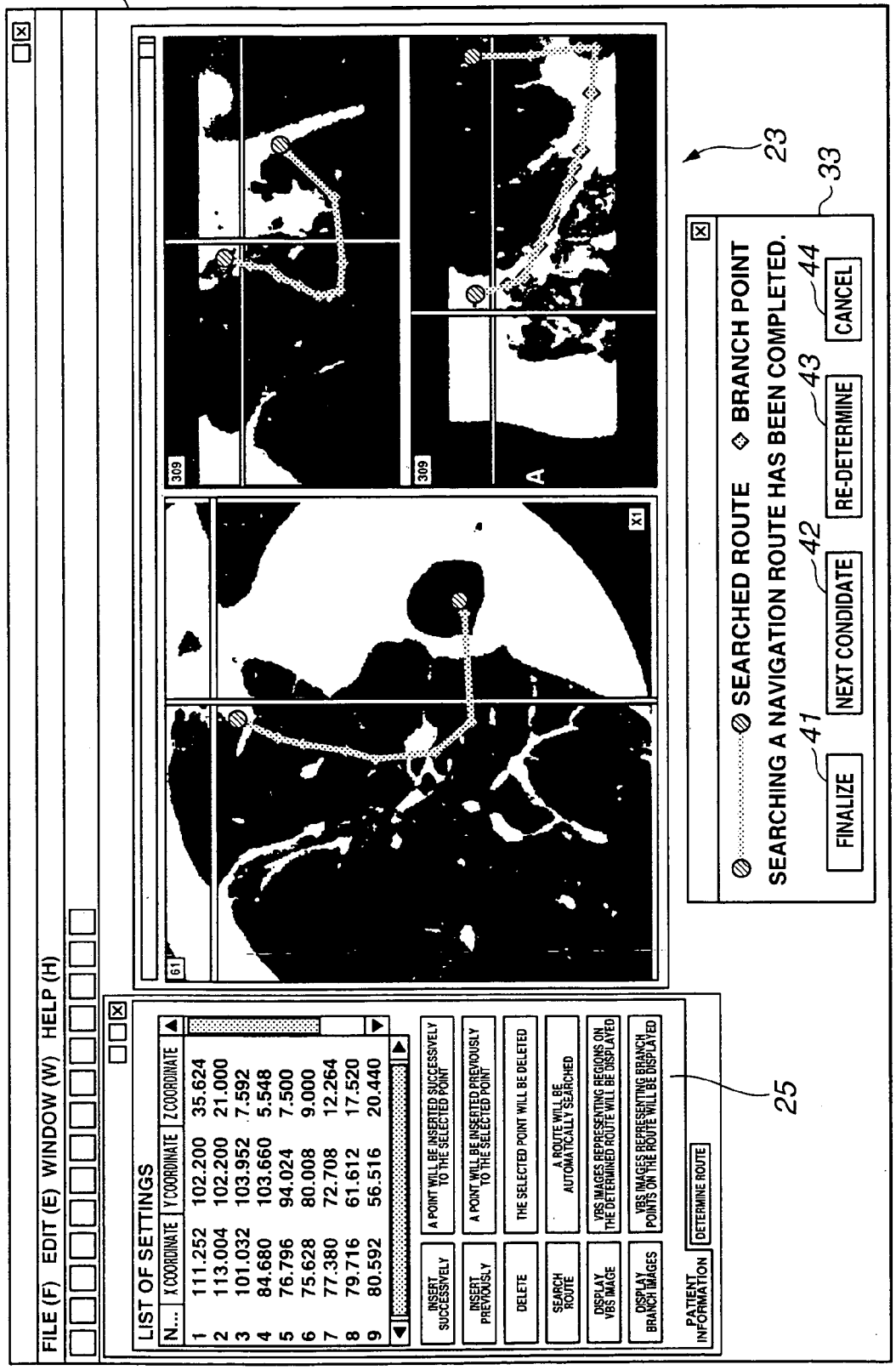
FIG. 9 is a third diagram showing the route determination screen in which the execution of the process described in FIG. 6 is performed.
Figure 10:
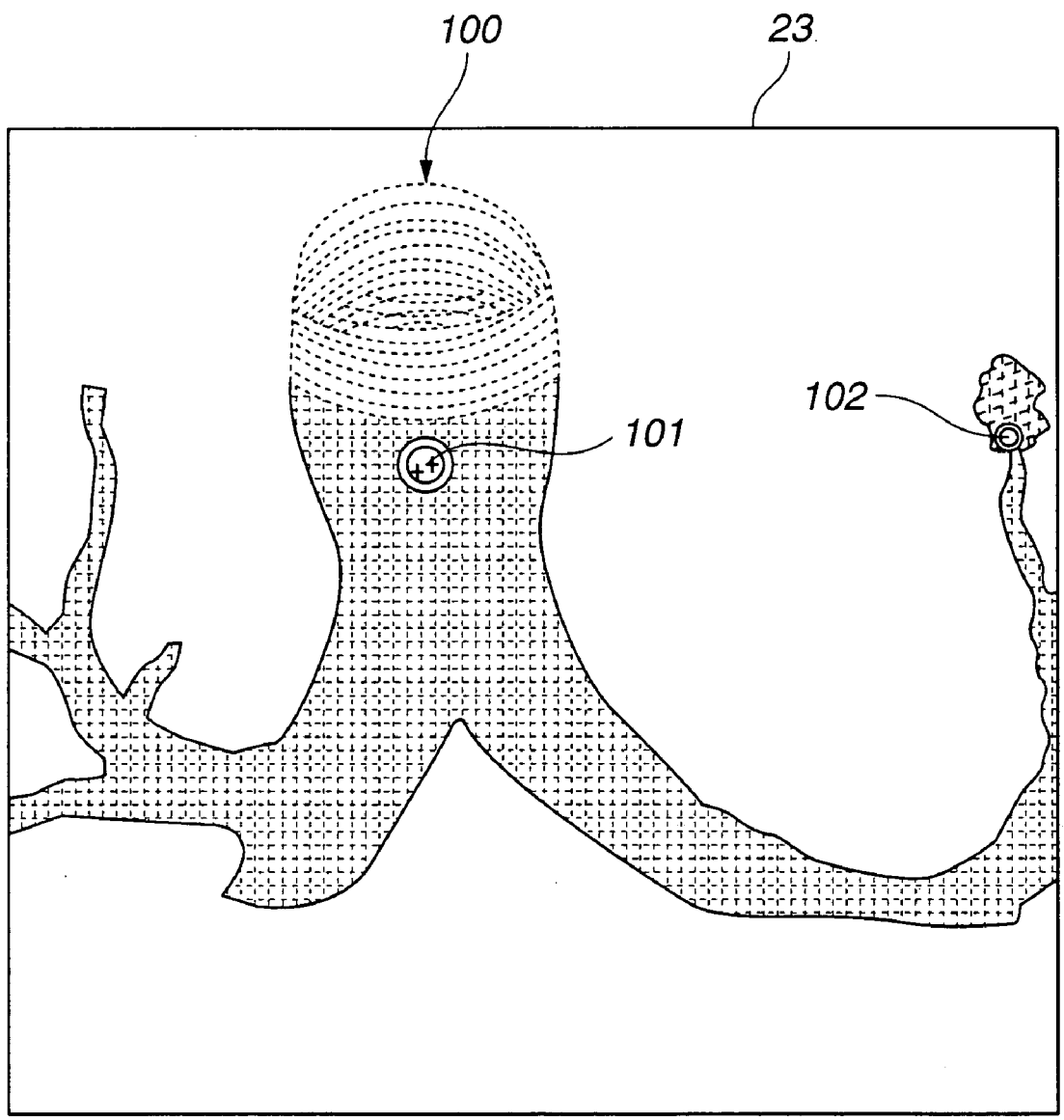
FIG. 10 is an explanatory diagram concerning a variant of route search to be executed by the bronchoscope navigation device shown in FIG. 1.
Figure 11:
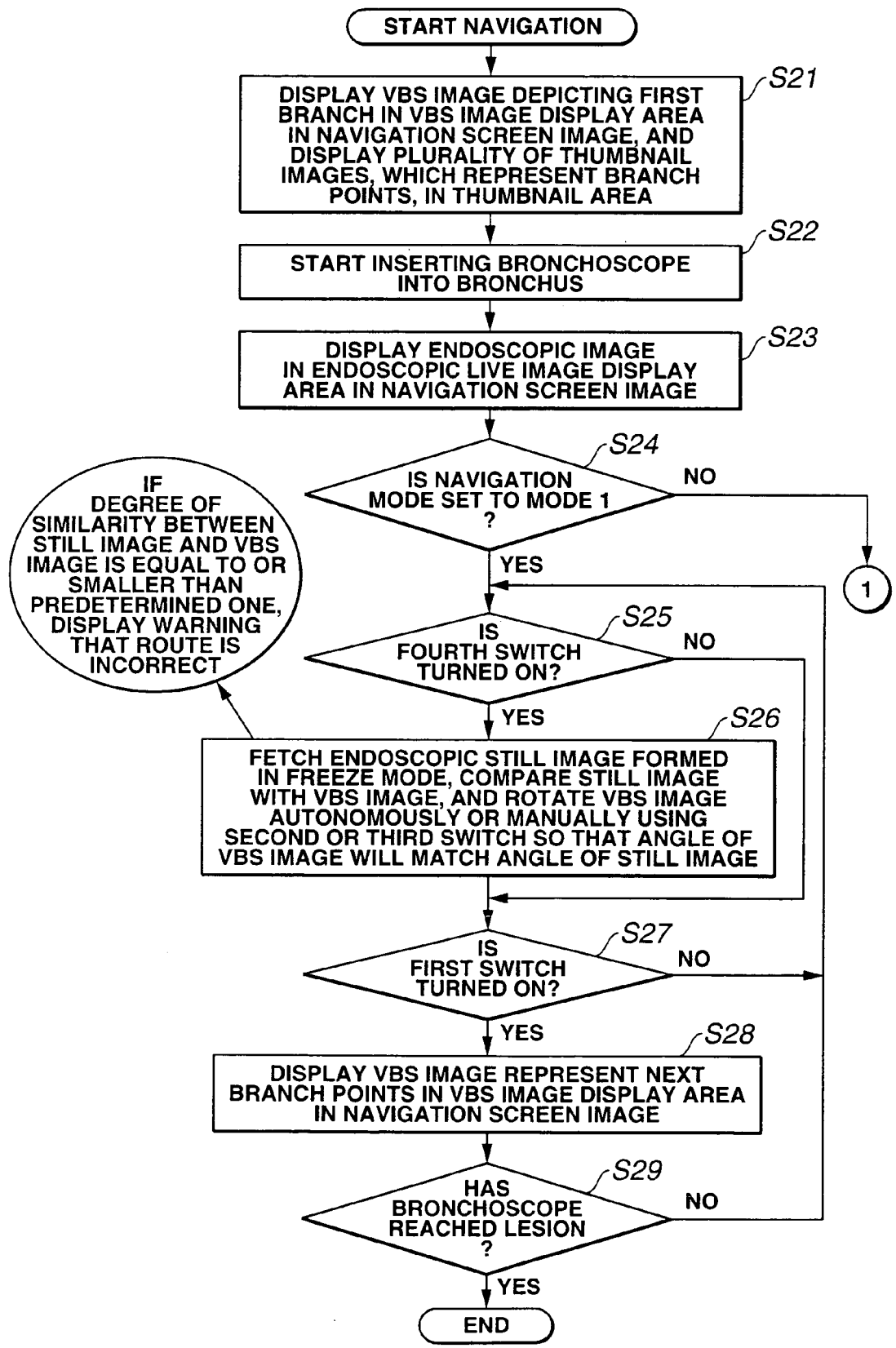
FIG. 11 is a first flowchart describing the flow of navigation to be executed by the bronchoscope navigation device shown in FIG. 1.
Figure 12:
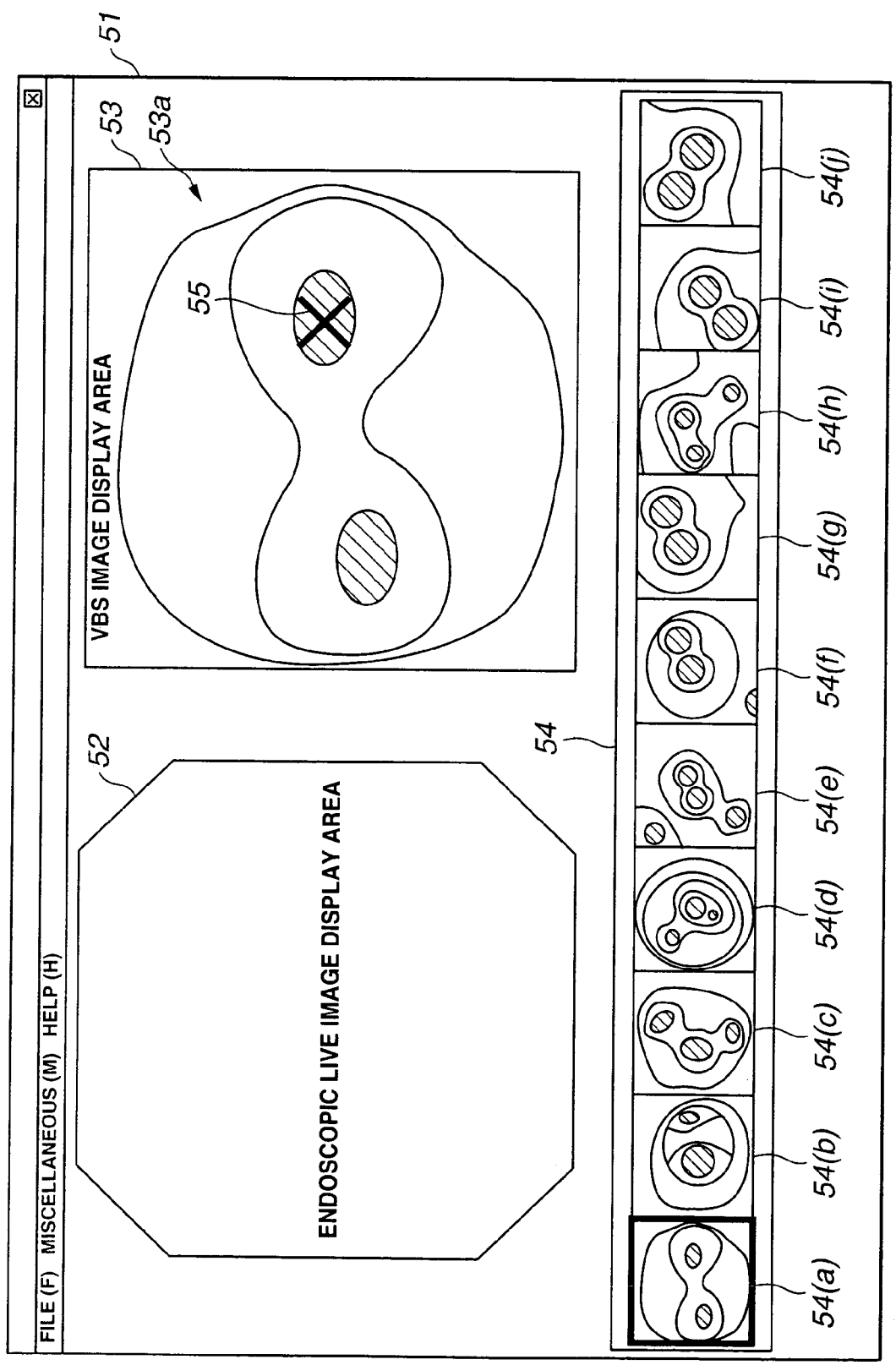
FIG. 12 is a first diagram showing a navigation screen in which the execution of the process described in FIG. 11 is performed.
Figure 13:
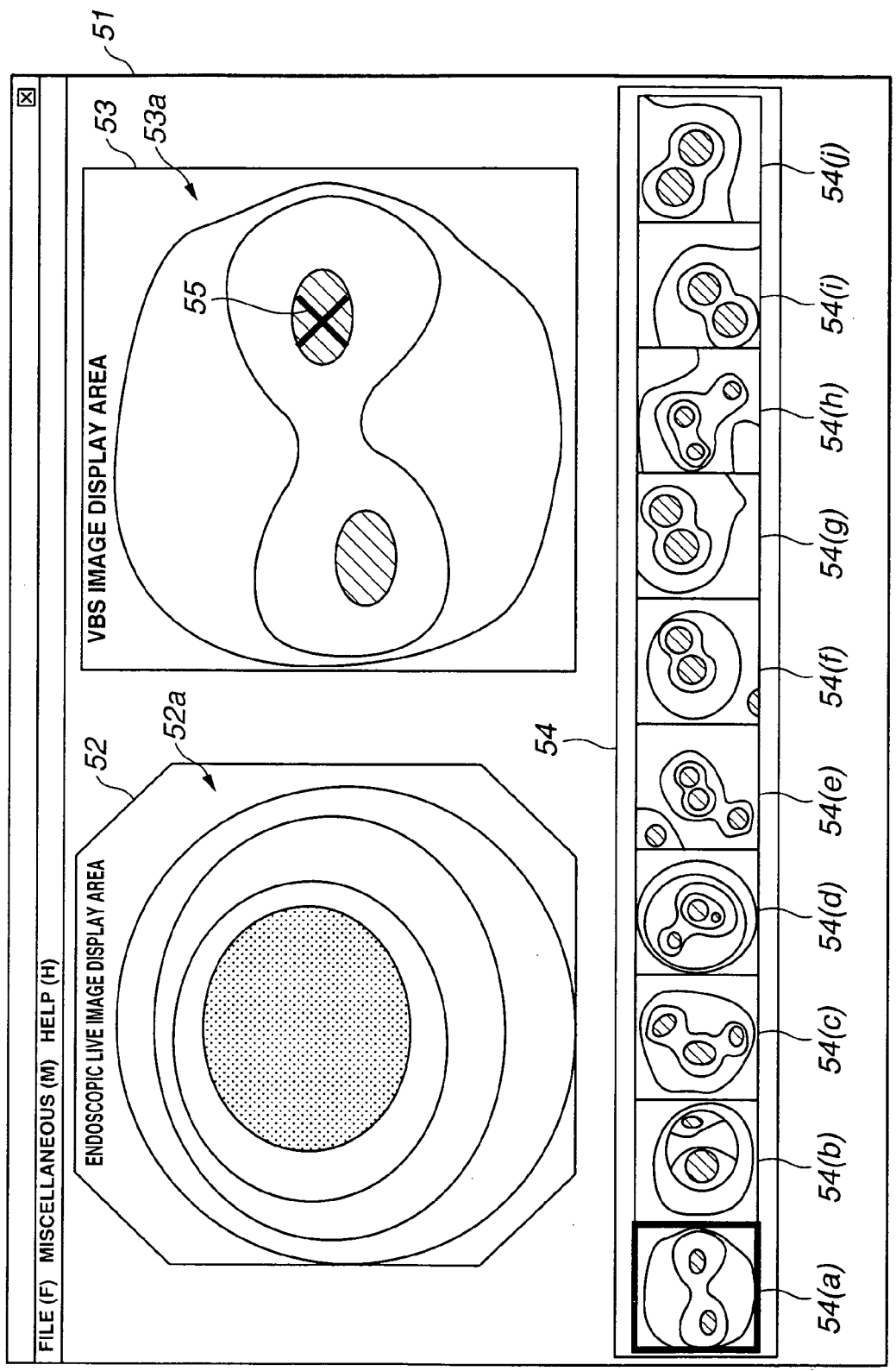
FIG. 13 is a second diagram showing a navigation screen in which the execution of the process described in FIG. 11 is performed.
Figure 14:
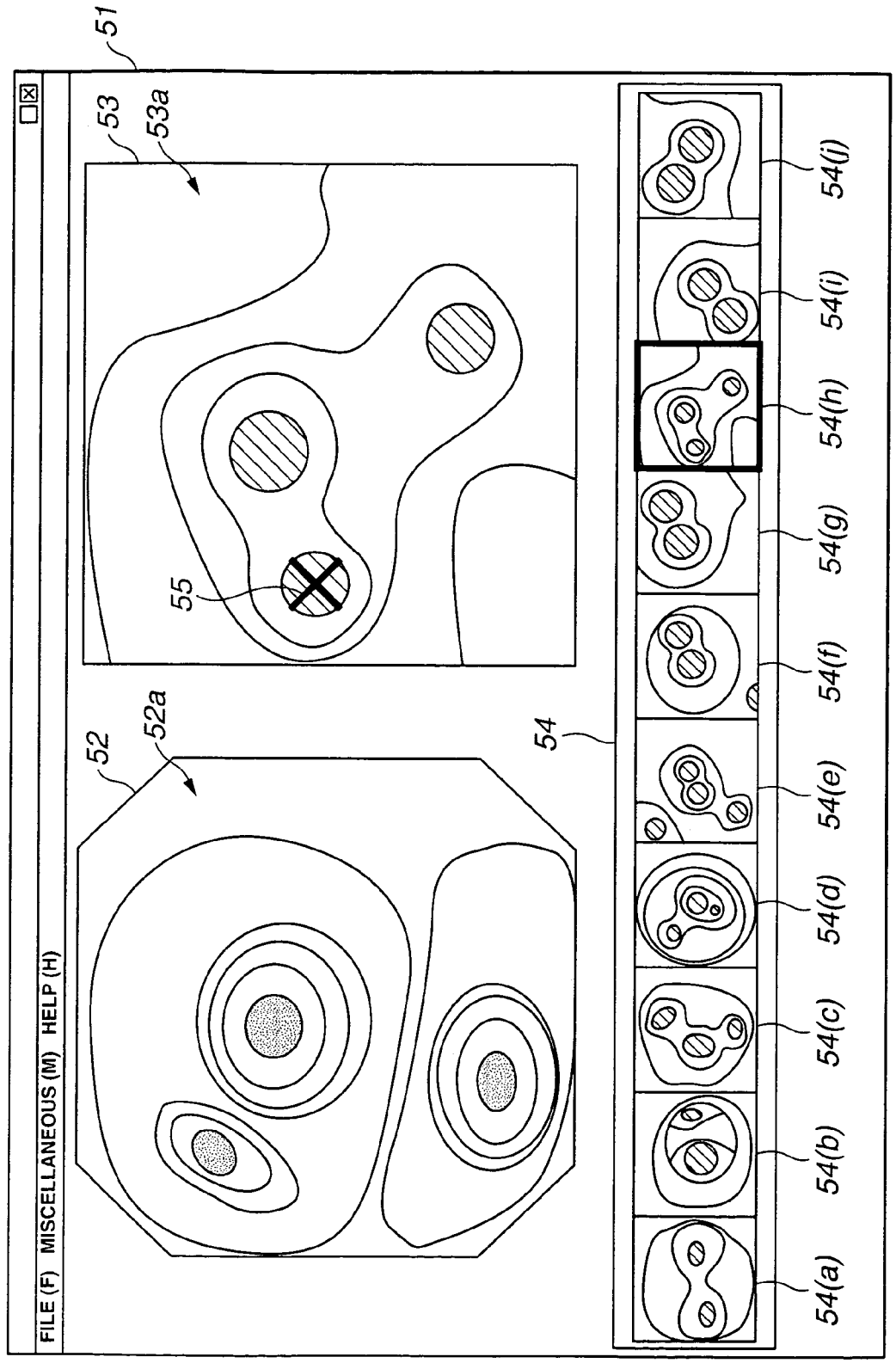
FIG. 14 is a third diagram showing a navigation screen in which the execution of the process described in FIG. 11 is performed.
Figure 15:
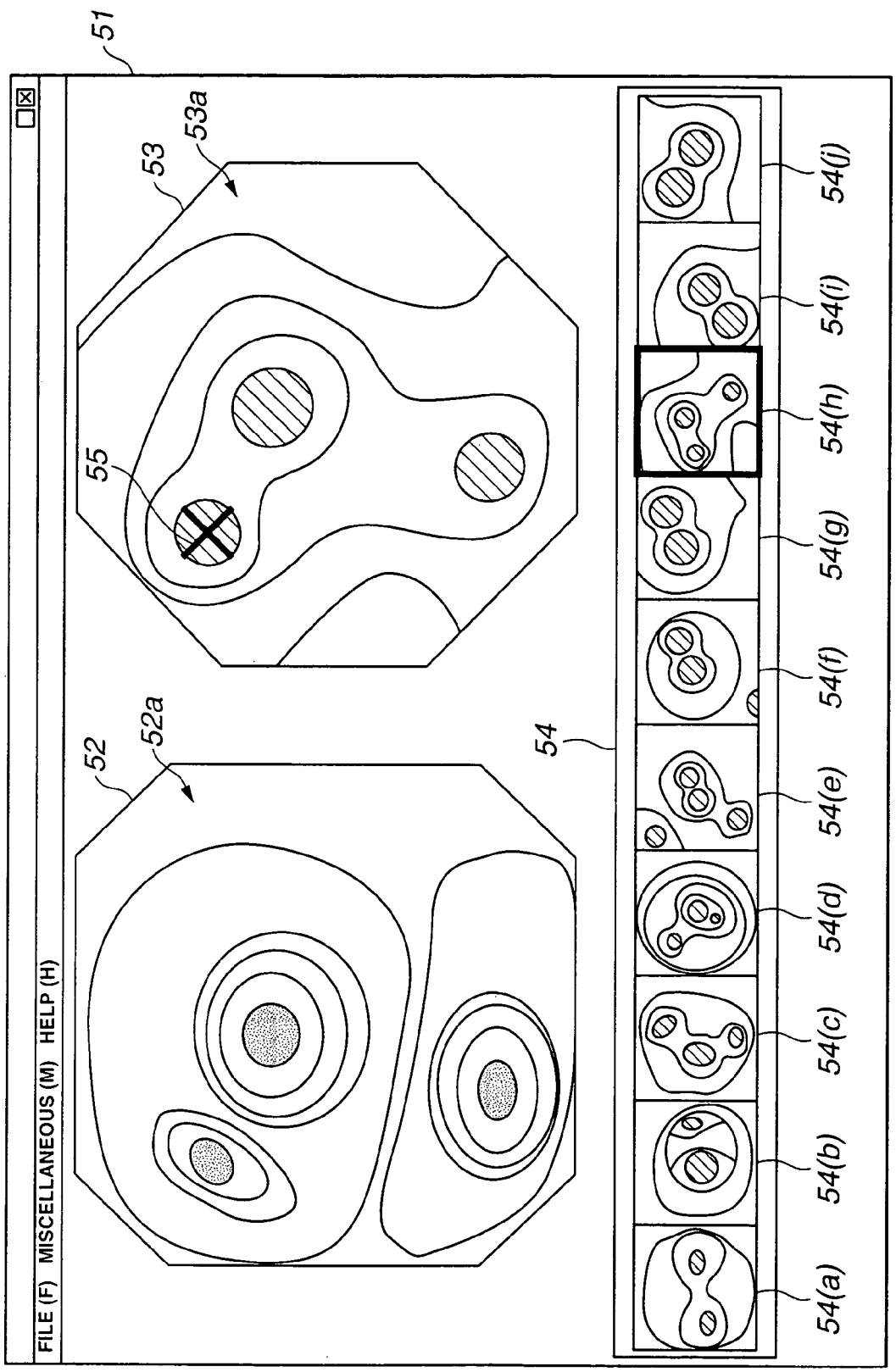
FIG. 15 is a fourth diagram showing a navigation screen in which the execution of the process described in FIG. 11 is performed.
Figure 16:
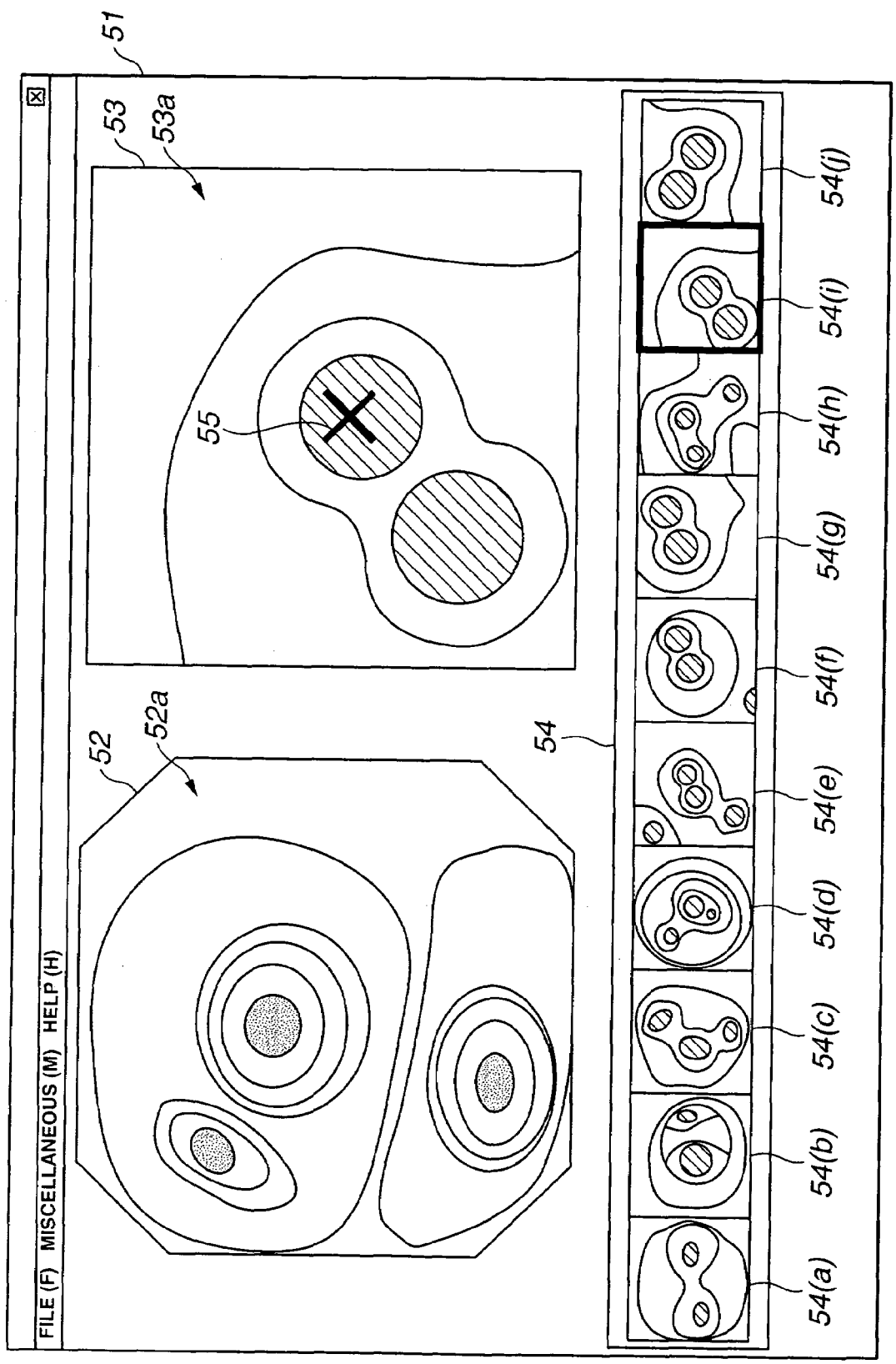
FIG. 16 is a fifth diagram showing a navigation screen in which the execution of the process described in FIG. 11 is performed.
Figure 17:
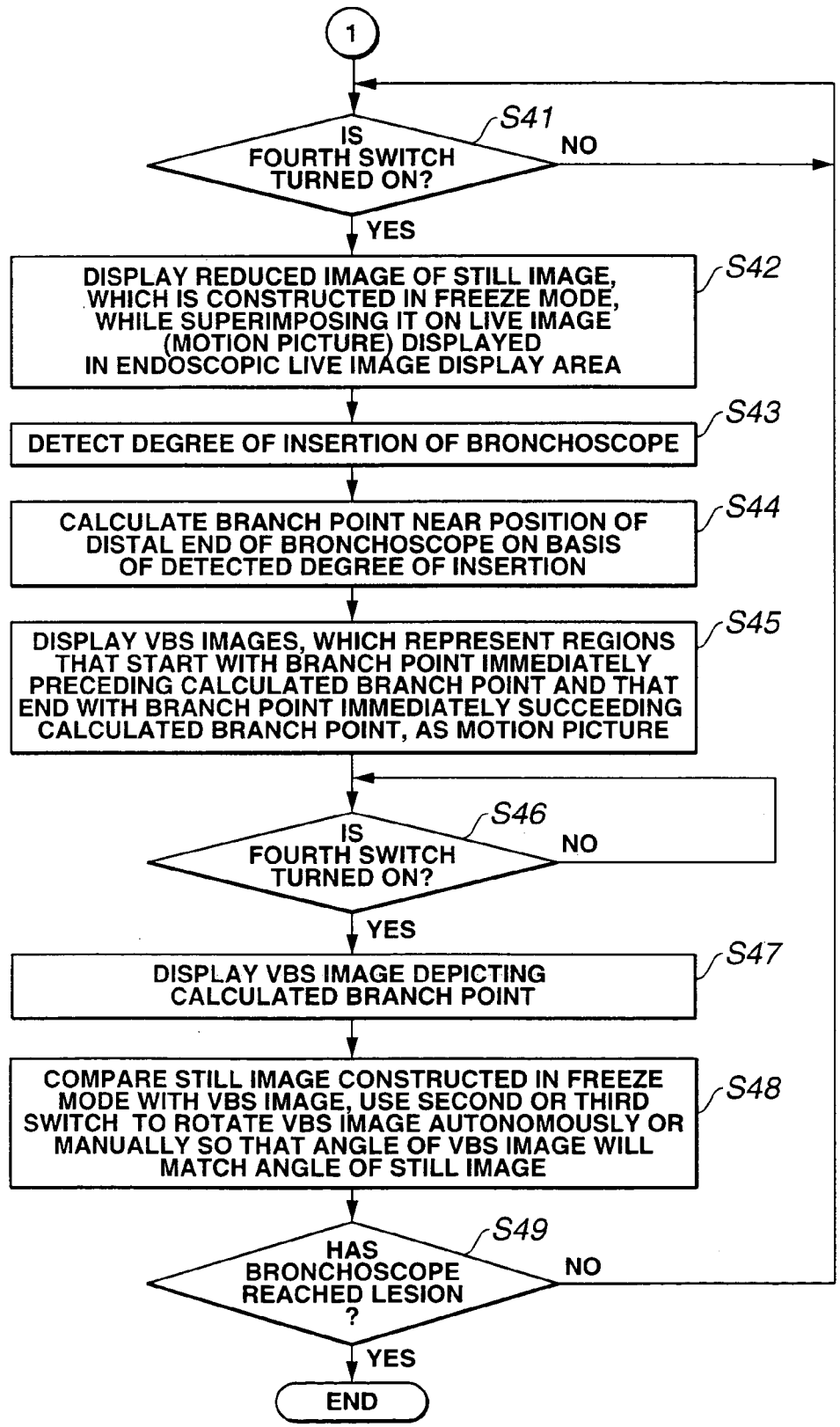
FIG. 17 is a second flowchart describing the flow of navigation to be executed by the bronchoscope navigation device shown in FIG. 1.
Figure 18:
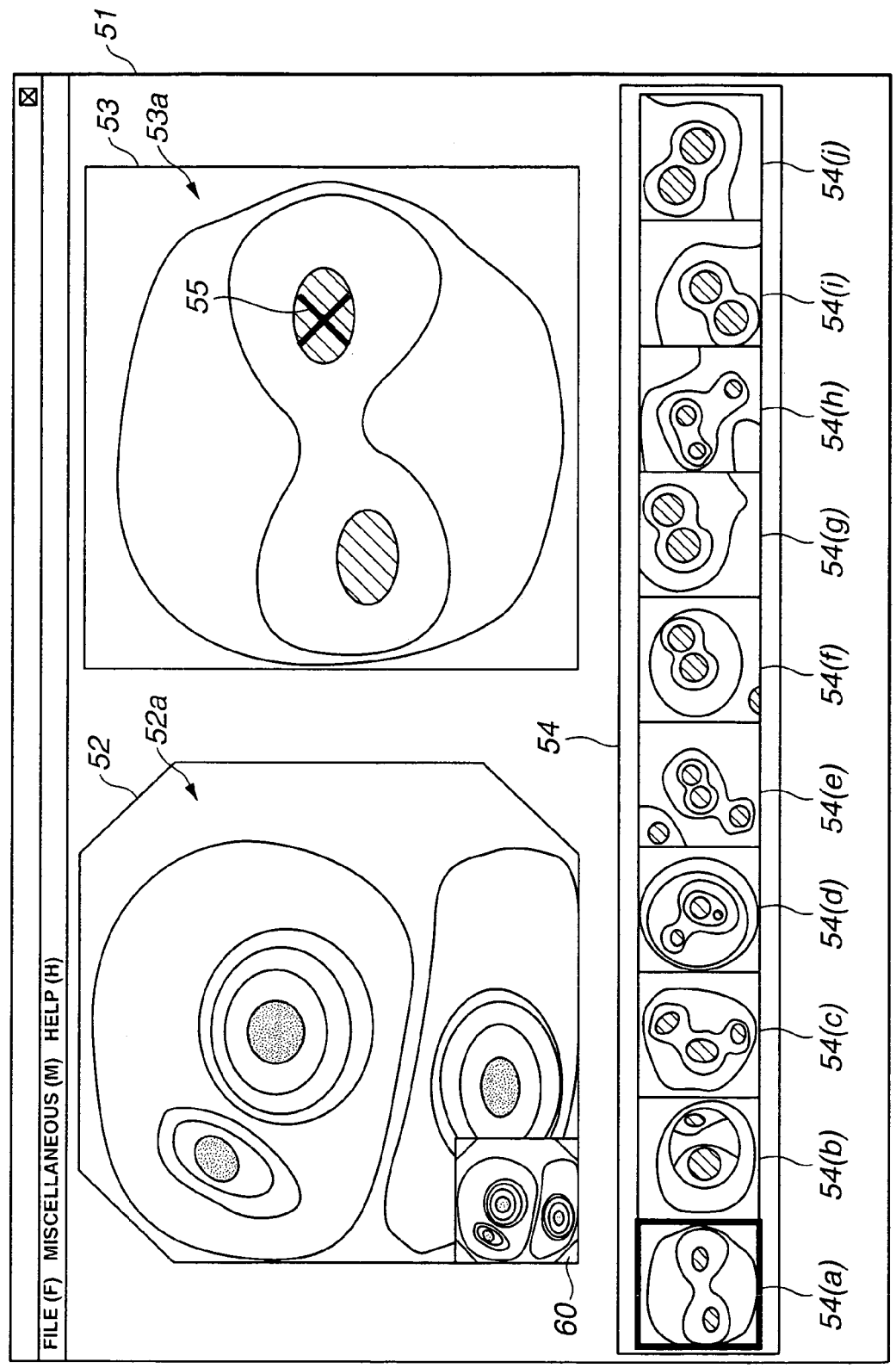
FIG. 18 is a first diagram showing a navigation screen in which the execution of the process described in FIG. 17 is performed.
Figure 19:
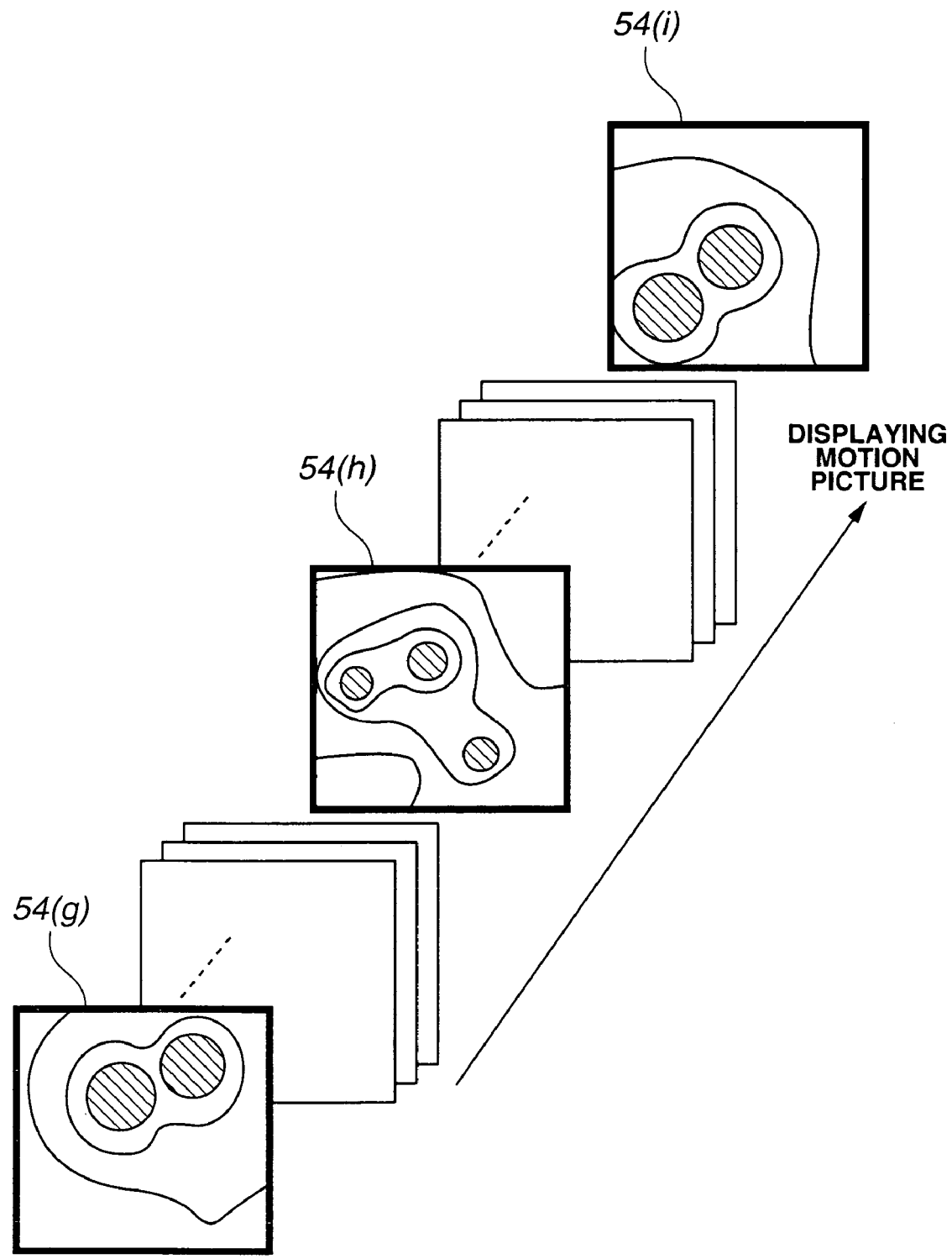
FIG. 19 is an explanatory diagram concerning a motion picture to be displayed by executing the process described in FIG. 17.
Figure 20:
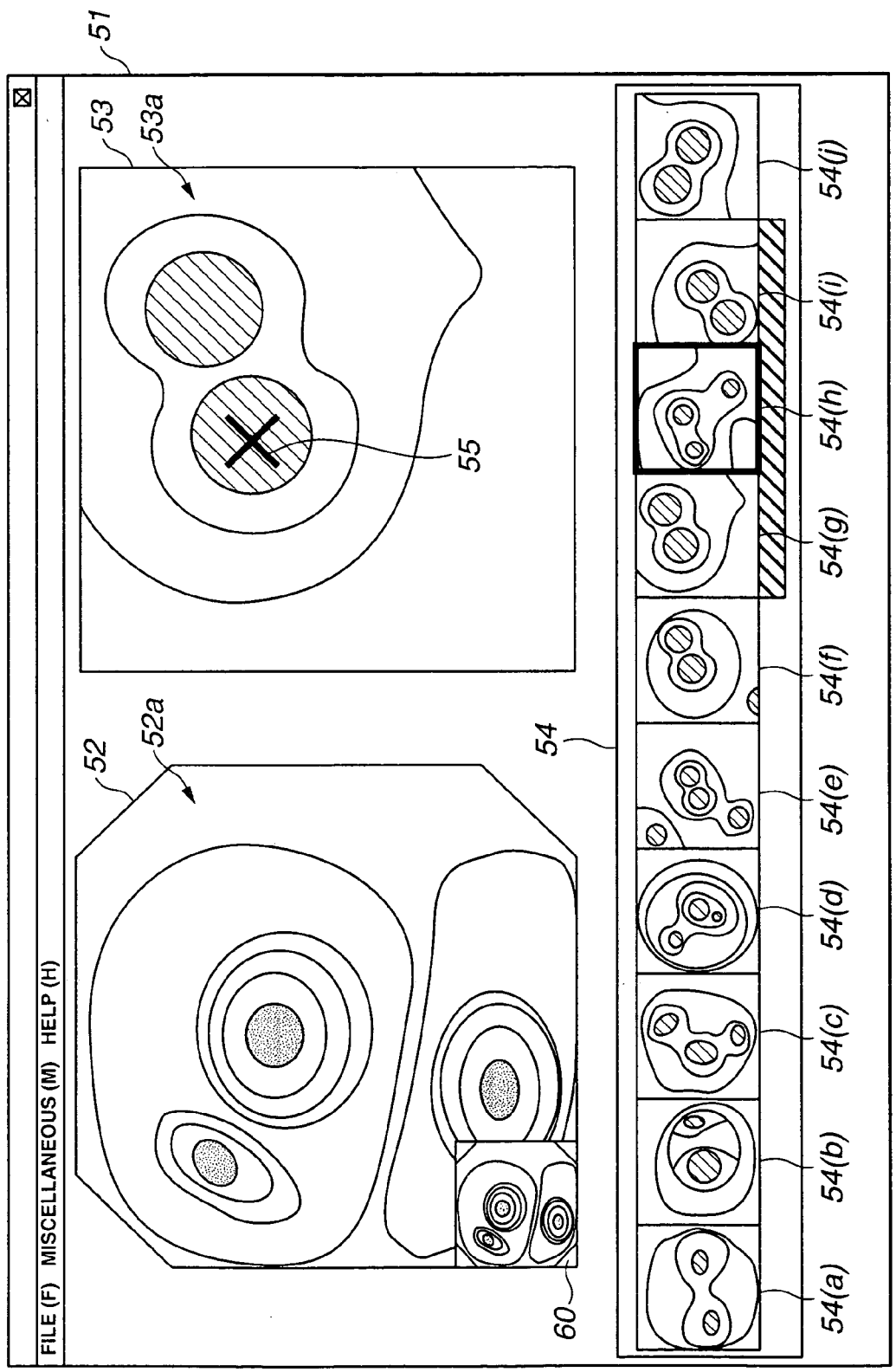
FIG. 20 is a second diagram showing the navigation screen in which the execution of the process described in FIG. 17 is performed.
Figure 21:
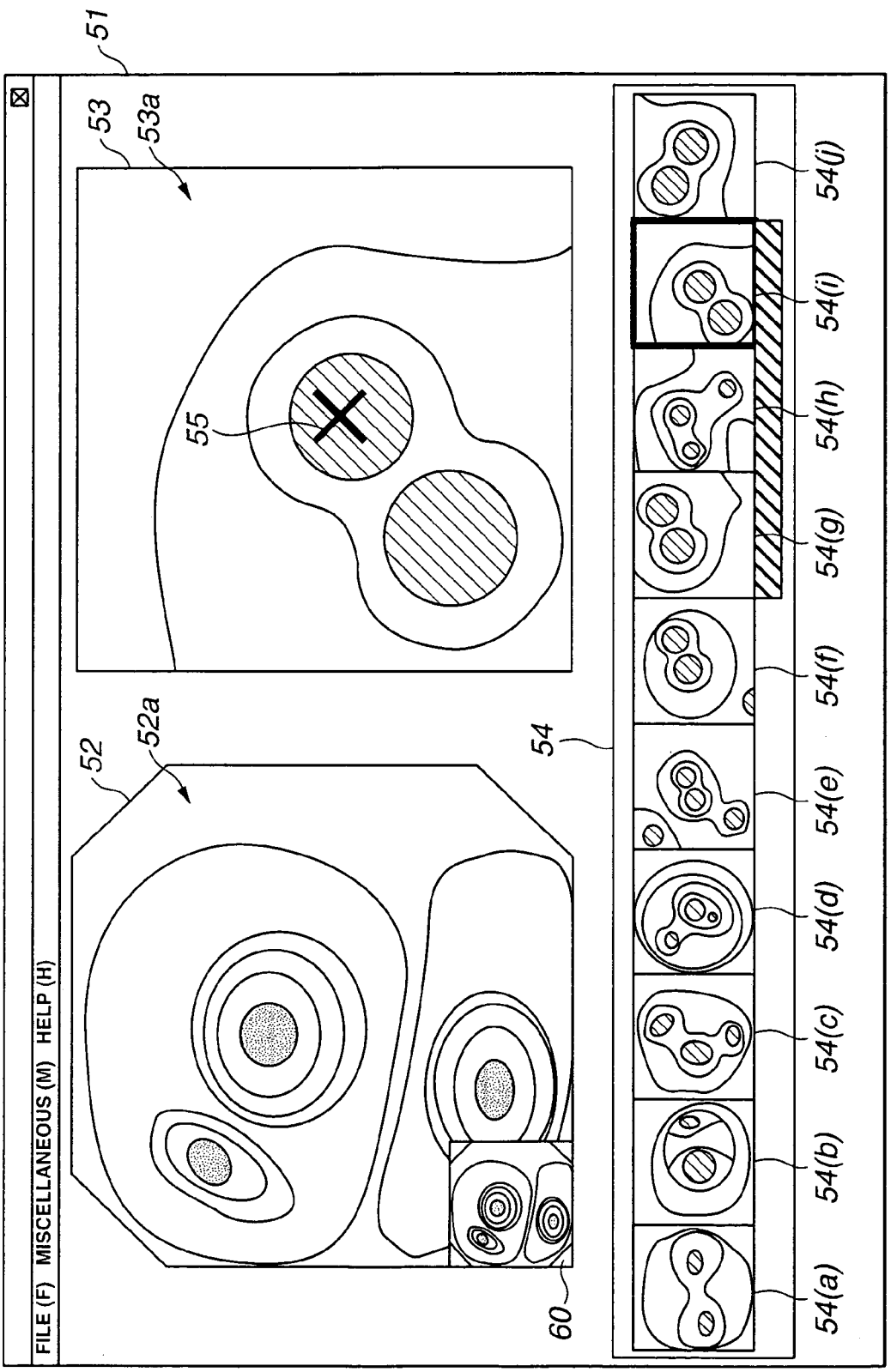
FIG. 21 is a third diagram showing the navigation screen in which the execution of the process described in FIG. 17 is performed.
Figure 22:
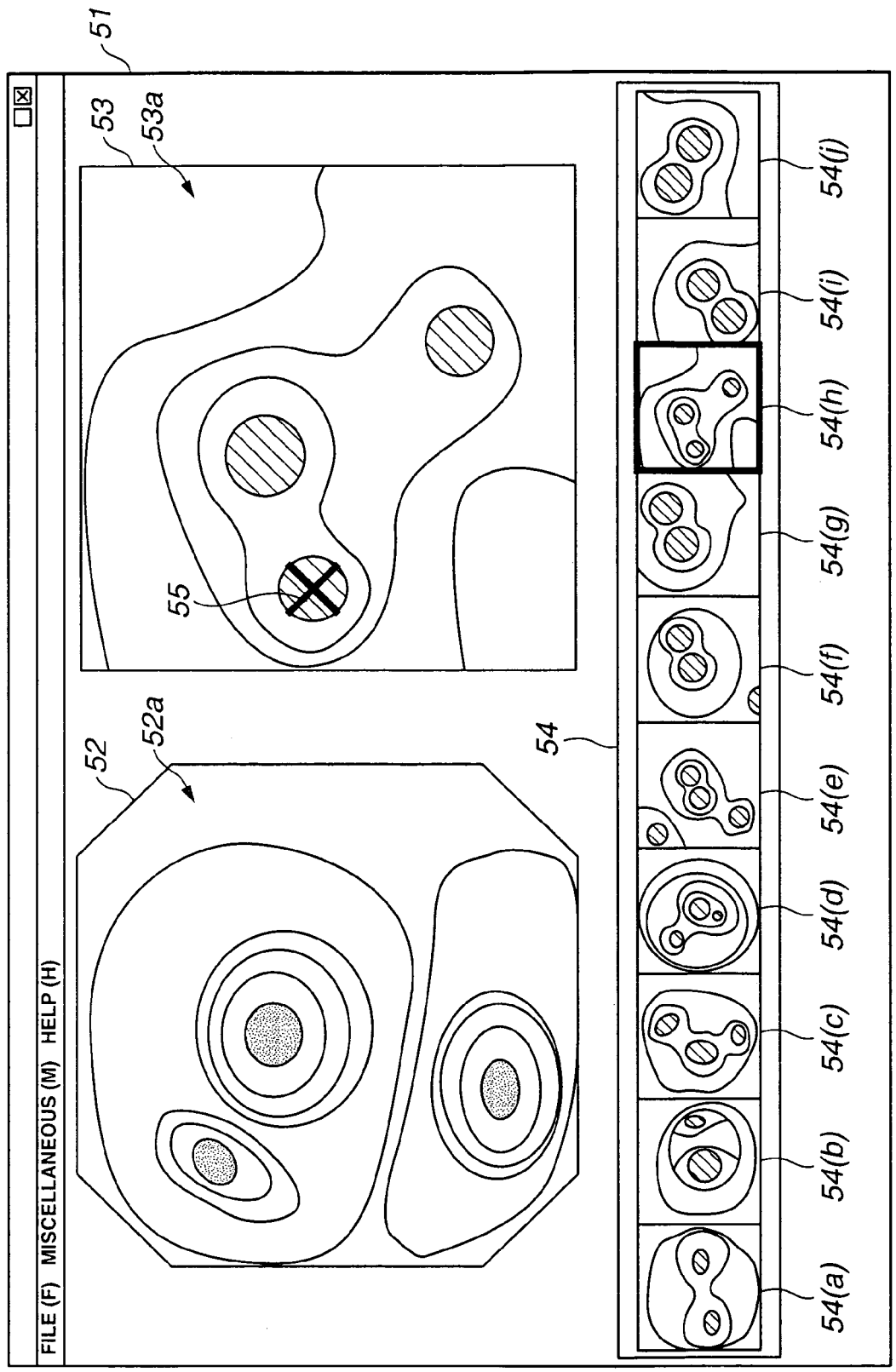
FIG. 22 is a third diagram showing the navigation screen in which the execution of the process described in FIG. 17 is performed.
Figure 23:
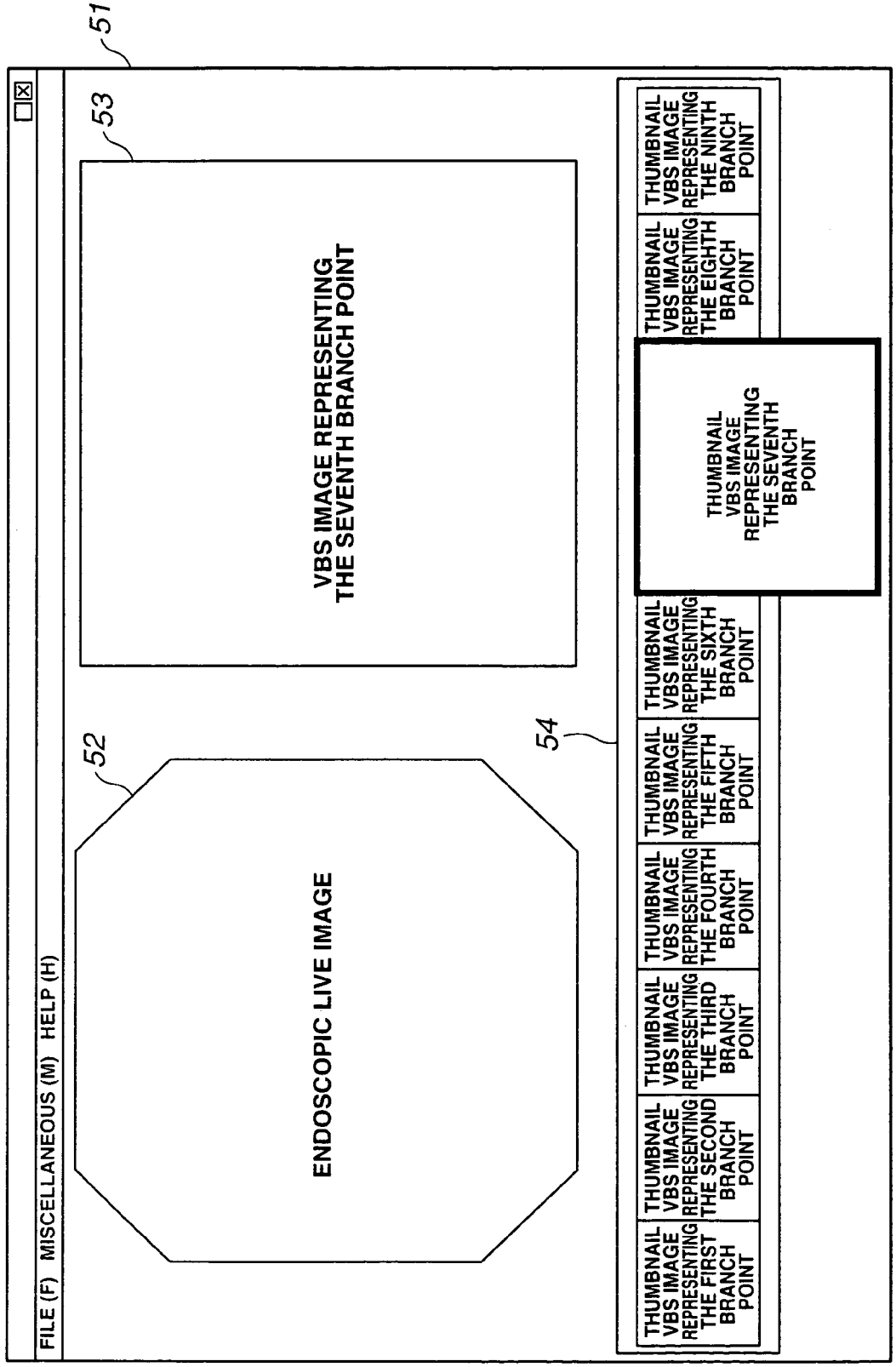
FIG. 23 shows a first variant of the navigation screen shown in FIG. 14.
Figure 24:
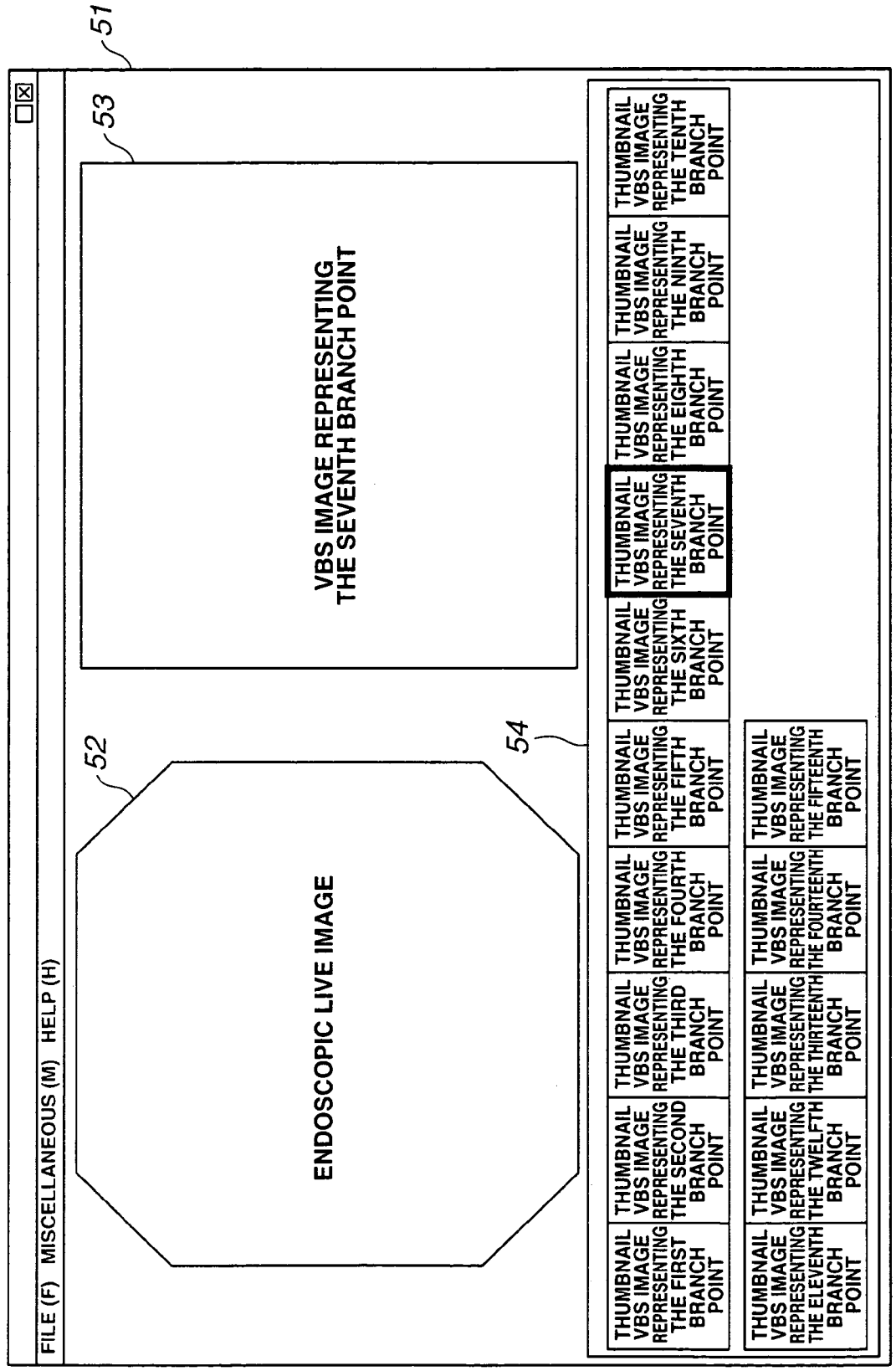
FIG. 24 is a second variant of the navigation screen shown in FIG. 14.
Figure 25:
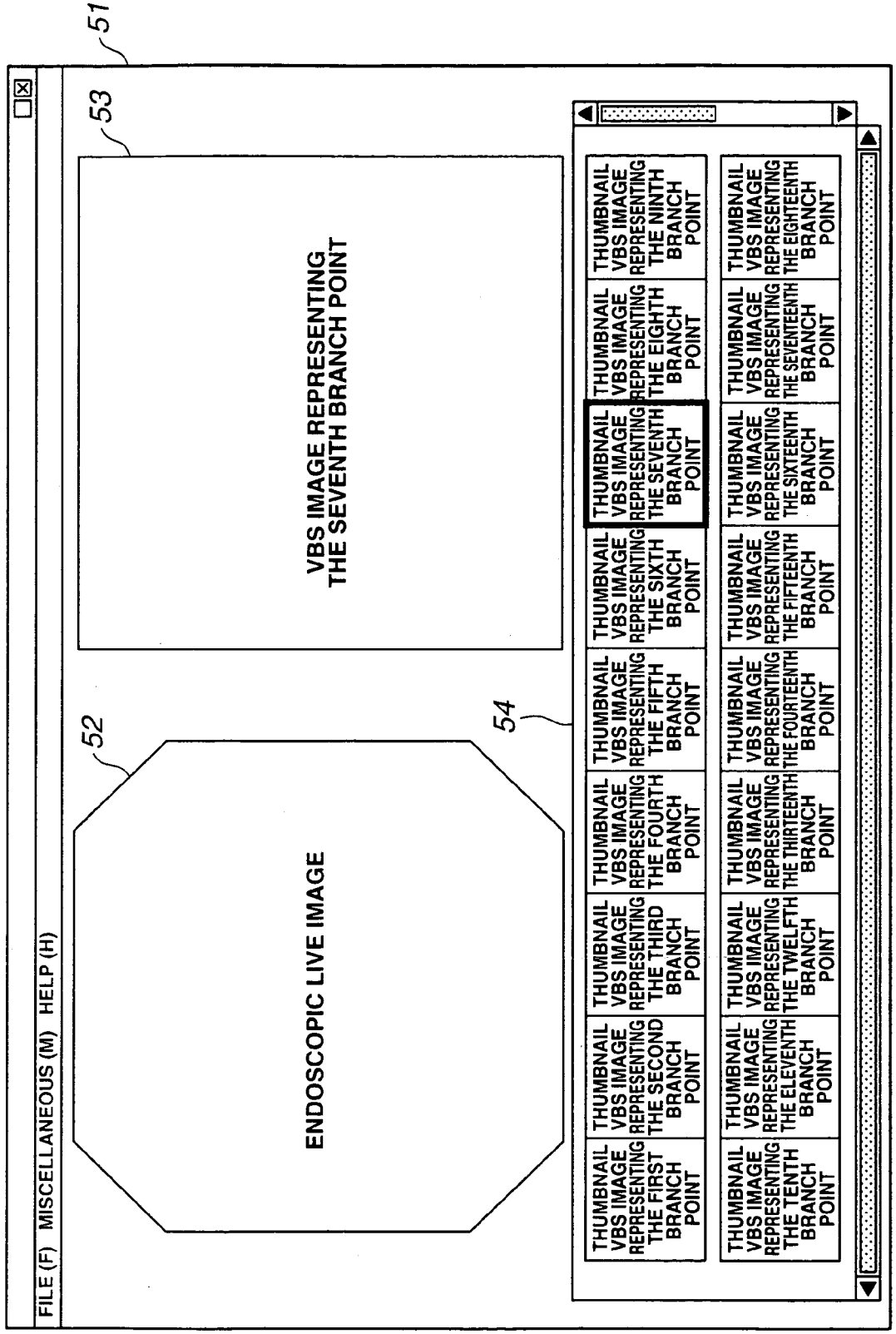
FIG. 25 is a third variant of the navigation screen shown in FIG. 14.
Figure 26:
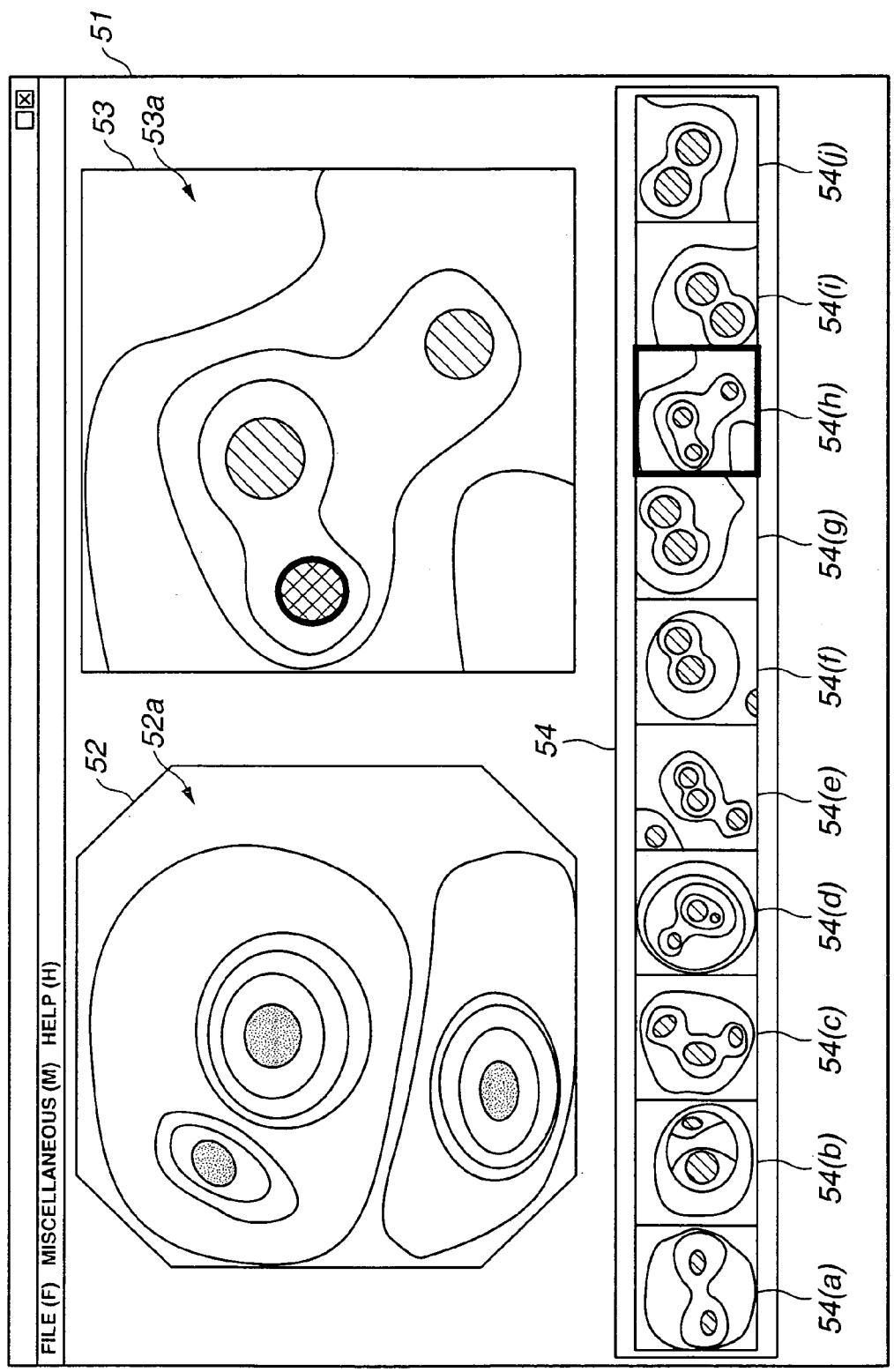
FIG. 26 is a fourth variant of the navigation screen shown in FIG. 14.
Figure 27:
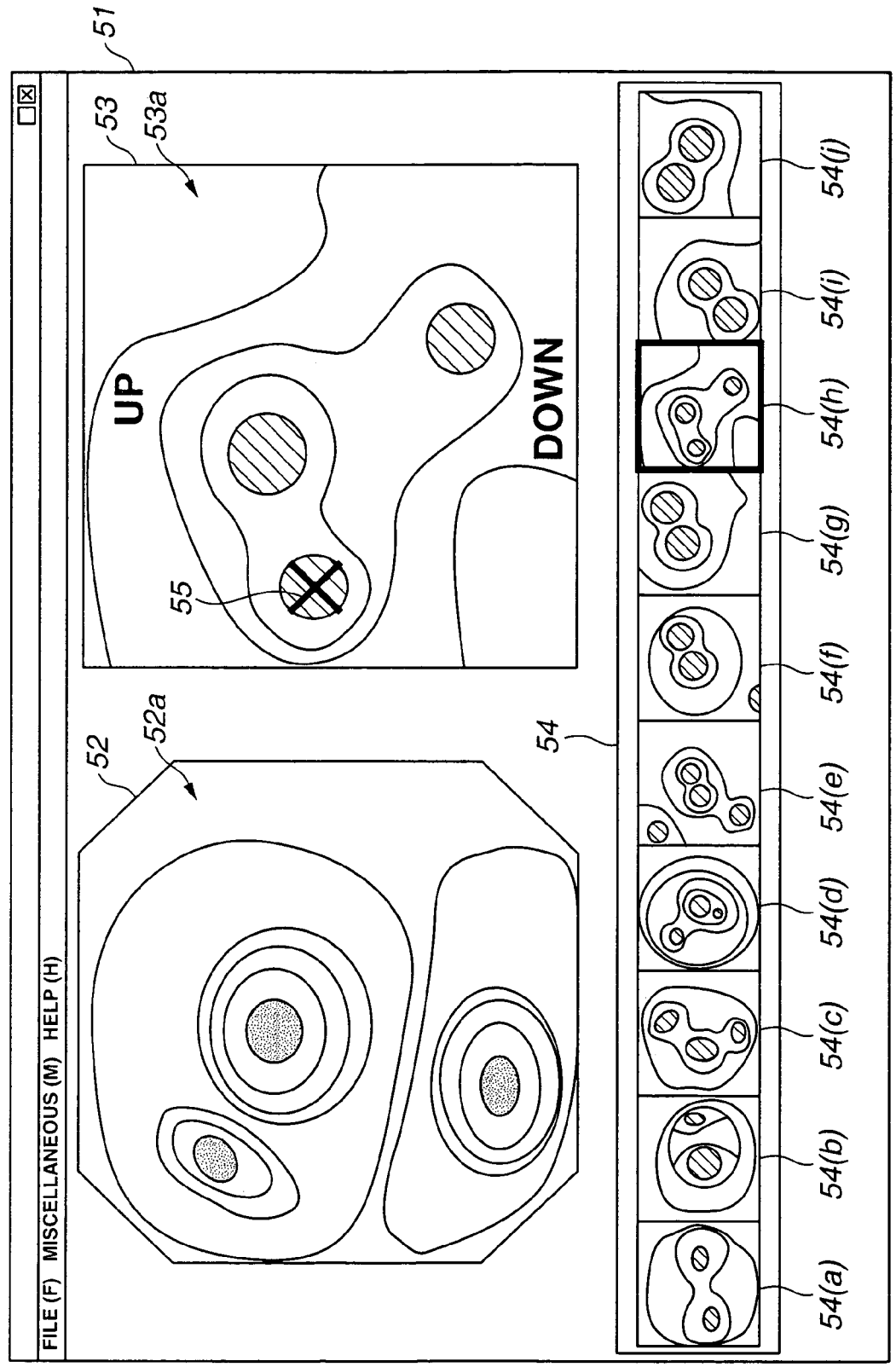
FIG. 27 is a fifth variant of the navigation screen shown in FIG. 14.
Figure 28:
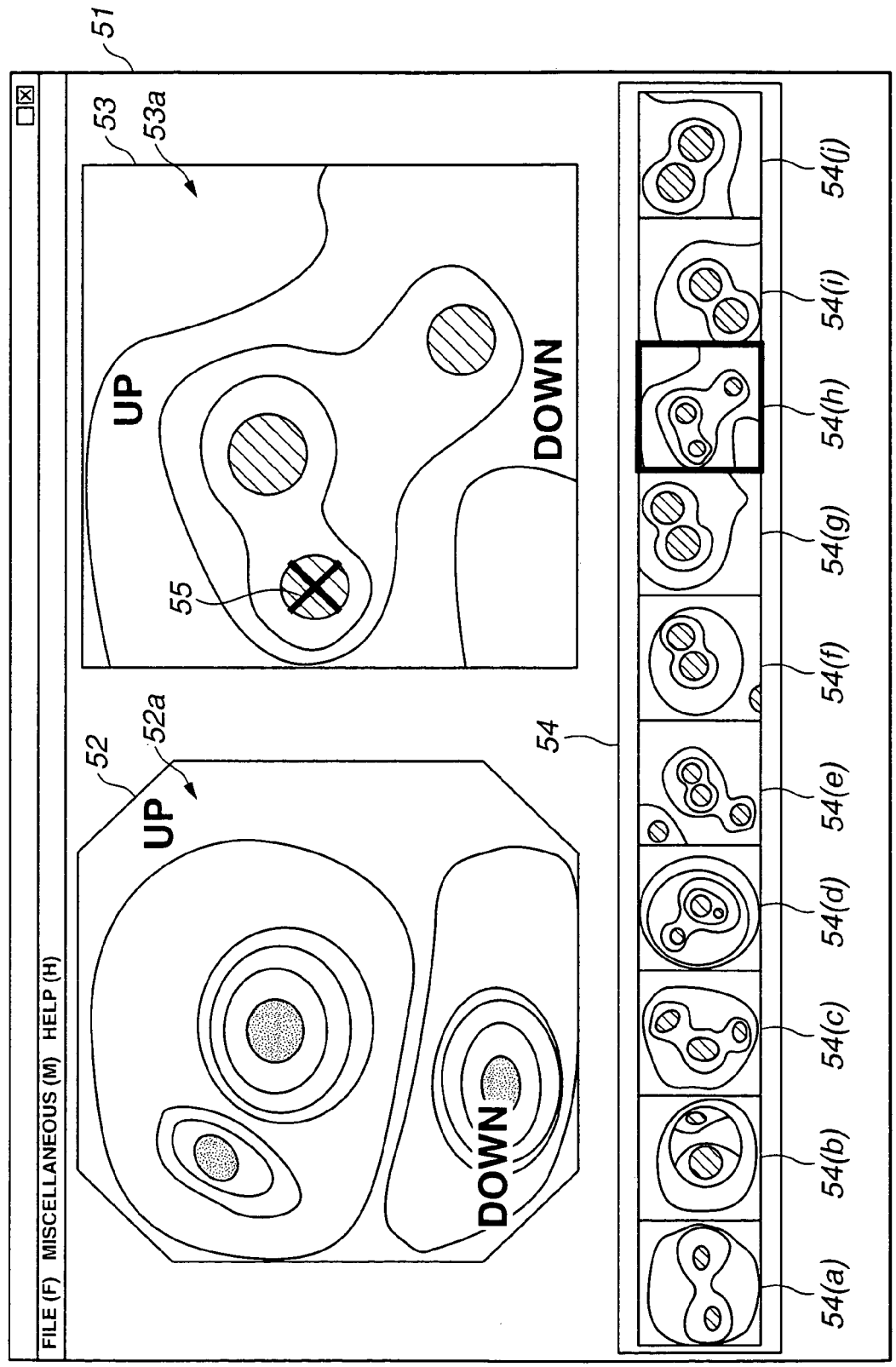
FIG. 28 is a sixth variant of the navigation screen shown in FIG. 14.
Figure 29:
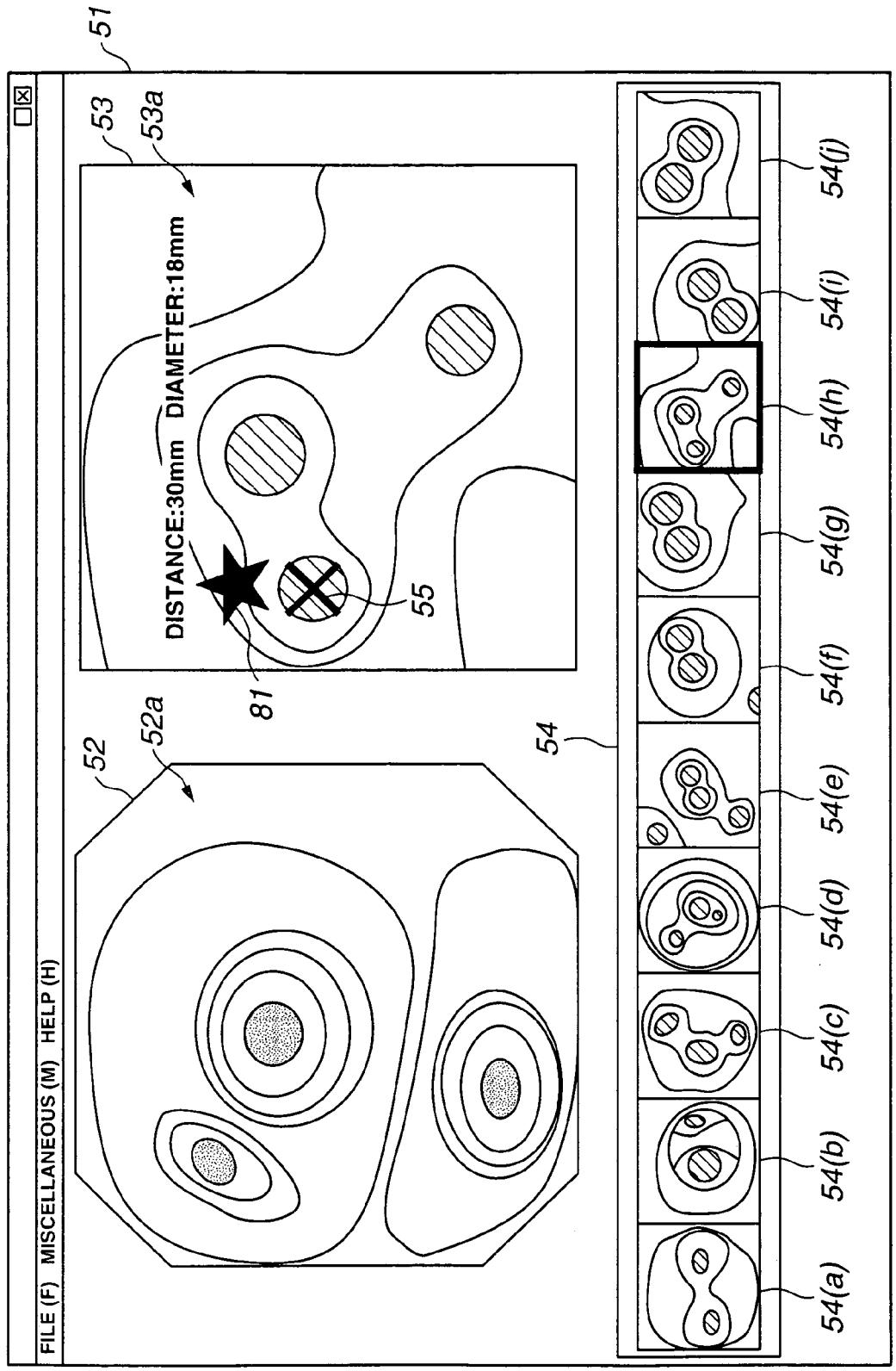
FIG. 29 is a seventh variant of the navigation screen shown in FIG. 14.
Figure 30:
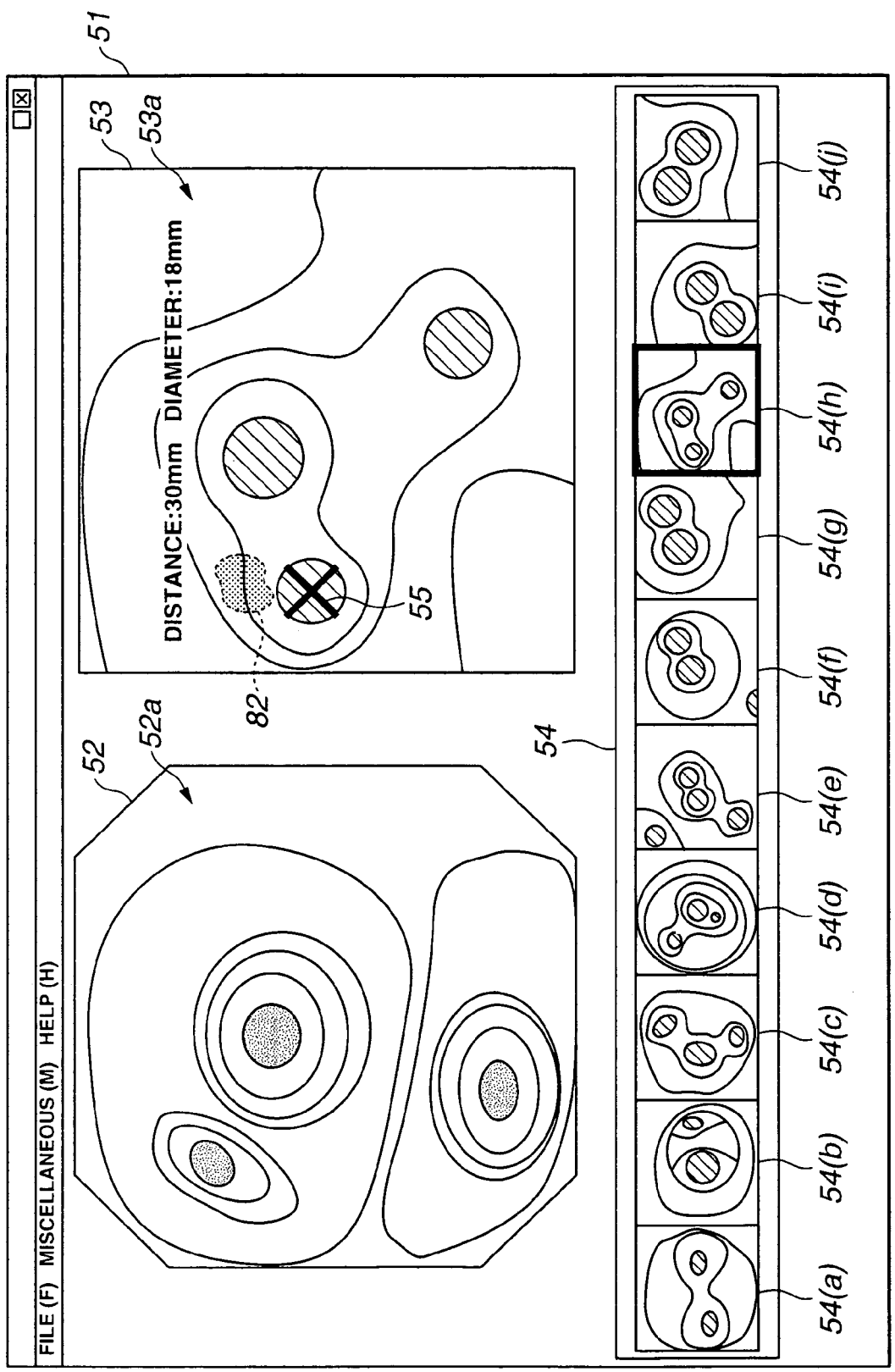
FIG. 30 is an eighth variant of the navigation screen shown in FIG. 14.
Figure 31:
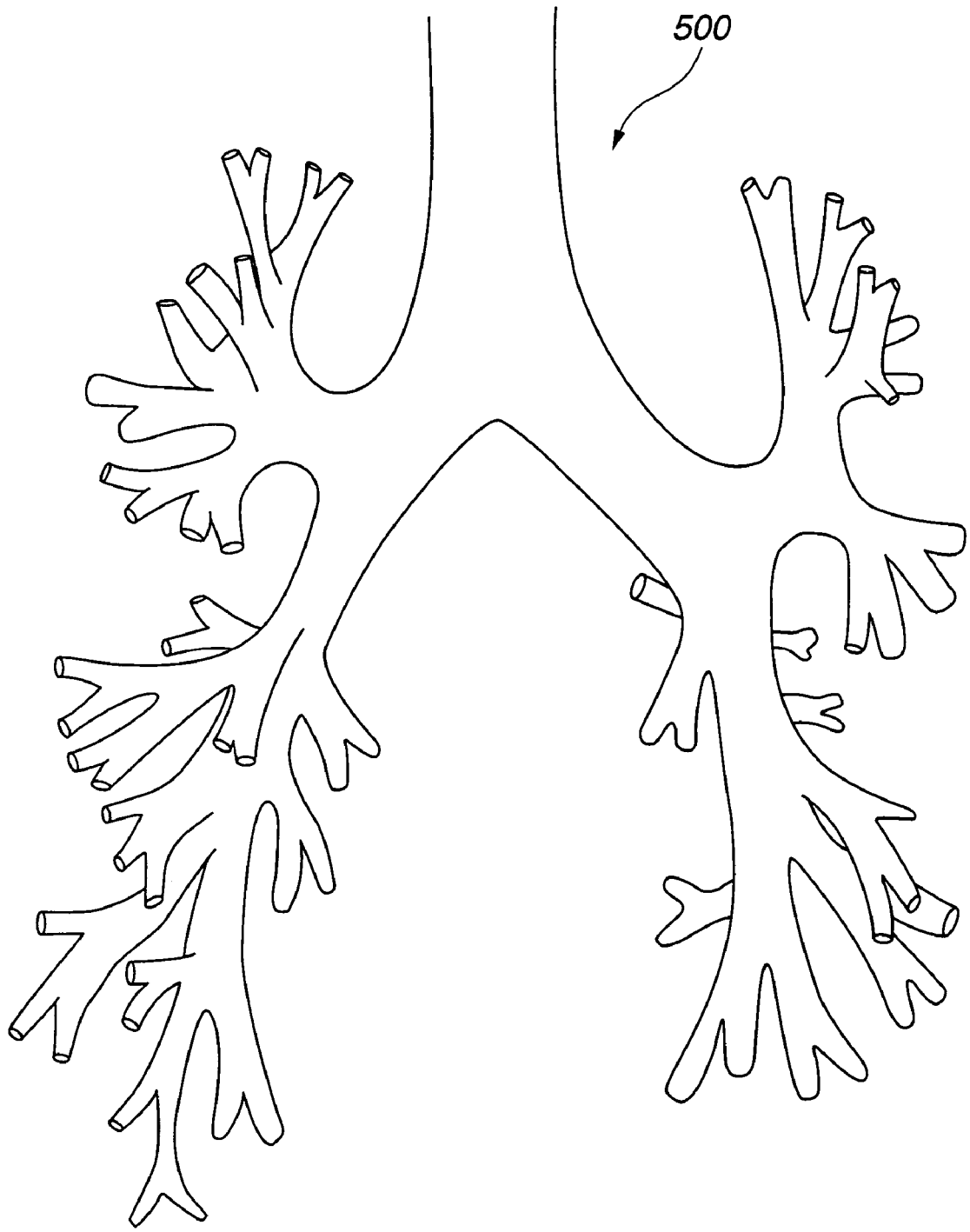
FIG. 31 shows the structure of bronchi.

FIG. 1 to FIG. 30 are concerned with an embodiment of the present invention. FIG. 1 shows the configuration of an endoscope device. FIG. 2 shows the configuration of an input unit shown in FIG. 1. FIG. 3 is a flowchart describing the flow of constructing navigation data to be performed by a bronchoscope navigation device shown in FIG. 1. FIG. 4 is a first diagram showing a route determination screen in which the execution of the process described in FIG. 3 is performed. FIG. 5 is a second diagram showing the route determination screen in which the execution of the process described in FIG. 3 is performed. FIG. 6 is a flowchart describing the flow of route determination to be executed at a step in the process described in FIG. 3. FIG. 7 is a first diagram showing a route determination screen in which the execution of the process described in FIG. 6 is performed. FIG. 8 is a second diagram showing the route determination screen in which the execution of the process described in FIG. 6 is performed. FIG. 9 is a third diagram showing the route determination screen in which the execution of the process described in FIG. 6 is performed. FIG. 10 is an explanatory diagram concerning a variant of route search to be executed by the bronchoscope navigation device shown in FIG. 1. FIG. 11 is a first flowchart describing the flow of navigation to be executed by the bronchoscope navigation device shown in FIG. 1. FIG. 12 is a first diagram showing a navigation screen in which the execution of the process described in FIG. 11 is performed. FIG. 13 is a second diagram showing a navigation screen in which the execution of the process described in FIG. 11 is performed. FIG. 14 is a third diagram showing a navigation screen in which the execution of the process described in FIG. 11 is performed. FIG. 15 is a fourth diagram showing a navigation screen in which the execution of the process described in FIG. 11 is performed. FIG. 16 is a fifth diagram showing a navigation screen in which the execution of the process described in FIG. 11 is performed. FIG. 17 is a second flowchart describing the flow of navigation to be executed by the bronchoscope navigation device shown in FIG. 1. FIG. 18 is a first diagram showing a navigation screen in which the execution of the process described in FIG. 17 is performed. FIG. 19 is an explanatory diagram concerning a motion picture to be displayed by executing the process described in FIG. 17. FIG. 20 is a second diagram showing a navigation screen in which the execution of the process described in FIG. 17 is performed. FIG. 21 is a third diagram showing a navigation screen in which the execution of the process described in FIG. 17 is performed. FIG. 22 is a third diagram showing a navigation screen in which the execution of the process described in FIG. 17 is performed. FIG. 23 shows a first variant of the navigation screen shown in FIG. 14. FIG. 24 shows a second variant of the navigation screen shown in FIG. 14. FIG. 25 is a third variant of the navigation screen shown in FIG. 14. FIG. 26 shows a fourth variant of the navigation screen shown in FIG. 14. FIG. 27 is a fifth variant of the navigation screen shown in FIG. 14. FIG. 28 is a sixth variant of the navigation screen shown in FIG. 14. FIG. 29 is a seventh variant of the navigation screen shown in FIG. 14. FIG. 30 is an eighth variant of the navigation screen shown in FIG. 14.

As shown in FIG. 1, an endoscope device 1 in accordance with the present embodiment comprises: a bronchoscope 2 that is inserted into the patient's bronchi in order to pick up images of the interiors of the bronchi or to biopsy a tissue of a lesion at the terminal of a bronchus; a degree-of-insertion detection unit 3 that detects a degree of insertion of the insertion unit of the bronchoscope 2 into the patient's body and that includes, for example, an encoder; an input unit 4 formed with a flexible sheet that realizes a plurality of switches in the form of a film and that is disposed on a proximal end of the bronchoscope 2; and a bronchoscope navigation device 6 that constructs virtual endoscopic images (hereinafter, VBS images) representing the interiors of bronchi on the basis of CT image data, synthesizes an endoscopic image (hereinafter, a live image), which is produced by the bronchoscope 2, with the VBS images according to an image pickup signal sent from the bronchoscope 2, a detection signal sent from the degree-of-insertion detection unit 3, and an input signal sent from the input unit 4, displays the resultant synthetic image on a monitor 5, and navigates the bronchoscope 2 through the bronchi.

Incidentally, the input unit 4 is formed on the proximal end of the bronchoscope 2. Alternatively, the input unit 4 may be formed with a footswitch.

The bronchoscope navigation device 6 comprises: a CT image data fetching unit 11 that fetches three-dimensional image data, which is constructed in a known CT system that is not shown and that produces X-ray tomographic images of a patient, via a transportable storage medium, for example, a magneto-optical (MO) disk or a digital versatile disk (DVD); a CT image data storage unit 12 in which three-dimensional image data fetched by the CT image data fetching unit 11 is stored; an MPR image construction unit 13 that constructs an MPR image on the basis of the three-dimensional image data stored in the CT image data storage unit 12; a route determination unit 14 that constructs a route determination screen that will be described later and that contains an MPR image constructed by the MPR image constructing unit, and determines a navigation route (hereinafter, simply, a route) along which the bronchoscope 2 is navigated through bronchi; a VBS image construction unit 15 that constructs VBS images, which represent successive regions along the route determined by the route determining unit 14, in units of a frame on the basis of the three-dimensional image data saved in the CT image data storage unit 12; a VBS image storage unit 16 in which VBS images constructed by the VBS image constructing unit 15 are stored; an image processing unit 17 that receives an image pickup signal sent from the bronchoscope 2, a detection signal sent from the degree-of-insertion detection unit 3, and an input signal sent from the input unit 4, and constructs a navigation screen that will be described later and that comprises a live image, a VBS image, and a plurality of thumbnail VBS images; an image display control unit 18 that displays the route determination screen, which is constructed by the route determination unit 14, and the navigation screen, which is constructed by the image processing unit 17, on the monitor 5; and a setting information input unit 19 including a keyboard and a pointing device to be used to enter setting information in the route determination unit 14.

Incidentally, the CT image data storage unit 12 and VBS image storage unit 16 may be realized with one hard disk, and the MPR image construction unit 13, route determination unit 14, VBS image construction unit 15, and image processing unit 17 may be realized with one arithmetic circuit. Moreover, the CT image data fetching unit 11 fetches CT image data from a transportable storage medium such as a MO disk or a DVD. Alternatively, when a CT system or an in-house server in which CT image data is preserved is connected on a in-house LAN, the CT image data fetching unit 11 may be realized with an interface circuit that can be connected on the in-house LAN. In this case, the CT image data can be fetched over the in-house LAN.

The input unit 4 has: as shown in FIG. 2, a Next VBS switch SW1 for use in directing update of a VBS image that is contained in a navigation screen and that represents each branch point of bronchi; an Auto Image Rotation switch SW2 for use in directing automatic rotation of a VBS image so that the direction of the VBS image will correspond to the direction of a live image; a Manual Image Rotation switch SW3 for use in directing rotation of a VBS image in units of a predetermined angle of rotation so that the direction of the VBS image will correspond to the direction of a live image; and a Freeze switch SW4 for use in directing fetching of a still image of a live image.

The operation of the present embodiment having the foregoing components will be described below.

As shown in FIG. 3, prior to observation or treatment performed using the bronchoscope 2, the bronchoscope navigation device 6 is activated. In the bronchoscope navigation device 6, at step S1, the CT image data fetching unit 11 fetches three-dimensional image data of a patient, which is constructed by a CT system. At step S2, the fetched three-dimensional image data is stored in the CT image data storage unit 12.

At step S3, the route determination unit 14 displays the route determination screen 21 like the one shown in FIG. 4 on the monitor 5. Patient information is selected through a patient information tag screen 22 contained in the route determination screen 21. With the selection, an MPR image is constructed from multiple different planar images, for example, three different multi-sectional images of a patient selected at step S4. At step S5, the MPR image 23 is contained in the route determination screen 21.

Incidentally, patient information is selected through the patient information tag screen 22 by entering a patient identifier (ID), with which a patient is identified, using the setting information input unit 19.

Next, at step S6, the setting information input unit 19 is used to select a route determination tag 24 (see FIG. 4) in the route determination screen 21. Consequently, a route determination tag screen 25 like the one shown in FIG. 5 appears in the route determination screen 21. Route determination that will be described later is then executed in order to determine a route along which the bronchoscope 2 is navigated through bronchi in order to help insert the bronchoscope 2.

After a route along which the bronchoscope is navigated in order to help insert the bronchoscope is determined, the VBS image construction unit 15 constructs successive VBS images, which represent regions along the entire route, in units of a frame. At step S8, the constructed VBS images are stored in the VBS image storage unit 16.

The bronchoscope navigation device 6 employed in the present embodiment can navigate the bronchoscope 2 through bronchi so as to help insert the bronchoscope 2 according to, for example, two navigation methods to be described later. The methods shall be implemented in mode 1 and mode 2 respectively. At step S9, the setting information input unit 19 is used to determine mode (navigation mode) for the route determination unit 14. The information of the navigation mode is transmitted to the image processing unit 17 via the route determination unit 14, and stored in both the image processing unit 17 and route determination unit 14.

By executing step S1 to step S9, preparations are made for navigation to be performed by the bronchoscope navigation device 6 for observation or treatment by the bronchoscope 2.

Now, route determination to be executed at step S6 will be described in conjunction with FIG. 6.

As shown in FIG. 6, during the route determination of step S6, the setting information input unit 19 is handled in order to click a Route Search button in the route setting tag screen 25 shown in FIG. 5. A start point entry direction window 31 that prompts a user to enter a start point of a route like the one shown in FIG. 7 is displayed in the route determination screen 21 at step S11. A start point is defined in one of the tomographic images constituting the MPR image 23 by moving a cursor 30 in the route determination screen 21. Once the start point is defined, the start point is indicated at corresponding positions in the other two tomographic images included in the MPR image 23. An end point entry direction window 32 that prompts a user to enter an end point of the route like the one shown in FIG. 8 is displayed in the route determination screen 21.

At step S12, similarly to the definition of the start point, an end point is defined in one of the tomographic images constituting the MPR image 23 by moving the cursor 30 in the route determination screen 21. Once the end point is defined, the end point is indicated at corresponding positions in the other two tomographic images included in the MPR image 23.

After the start point and end point are defined, the route determination unit 14 searches a route that links the start point and end point and that runs through bronchi. The bronchi have complex paths. The route that links the start point and end point and that runs through bronchi cannot therefore always be determined unconditionally. At step S13, the route determination unit 14 therefore searches a first candidate for the route that links the start point and end point and that runs through bronchi.

The route determination unit 14 then displays the route searched at step S14 by superimposing the route on the MPR image 23 contained in the route determination screen 21 as shown in FIG. 9. Moreover, a route finalization window 33 that prompts a user to finalize a route is displayed.

The route finalization window 33 comprises: a Finalize Route button 41 for use in directing finalization of a searched route; a Search Next Candidate button 42 for use in directing search of the next candidate for a route; a Re-determine Route button 43 for use in redefining a start point and an end point; and a Cancel button 44 for use in canceling route search.

At step S15, it is judged whether the Search Next Candidate button 42 is clicked. If the Search Next Candidate button 42 is clicked, the next candidate for a route is automatically searched at step S16. Control is then passed to step S17. If the Search Next Candidate button 42 is not clicked, control is passed to step S18. At step S17, it is judged whether the next candidate is found as a result of search. If the next candidate is unfound, the warning that the next candidate for a route is unfound is displayed, and control is returned to step S13. If the next candidate is found, control is returned to step S14.

At step S18, it is judged whether the Re-determine Route button 43 is clicked. If the Re-determine Route button 43 is clicked, control is returned to step S11. If the Re-determine Route button 43 is not clicked, control is passed to step S19.

At step S19, it is judged whether the Finalize Route button 41 is clicked. If the Finalize Route button 41 is not clicked, control is returned to step S15. If the Finalize Route button 41 is clicked, control is passed to step S20. At step S20, a route and positions of branch points on the route are determined, and control is returned to step S7 in FIG. 6.

After the three-dimensional position information of the branch points on the route is determined at step S20, the order numbers of the branch points lying on the course to be steered in order to insert the bronchoscope from a start point 101 to an end point 102 are appended to the VBS images representing the branch points. The VBS images are then stored in the VBS image storage unit 16 at step S8. Consequently, the VBS image data representing each branch point includes virtual image data that represents the branch portion, three-dimensional position information concerning the branch portion, and information of an order number assigned to the branch portion lying on the selected course to be steered in order to insert the bronchoscope.

Incidentally, route search to be performed using an MPR image has been described. An image 100 constructed using a volume rendering technique as shown in FIG. 10 may be used to designate the start point 101 and end point 102 for the purpose of route search.

A description will be made of navigation of the bronchoscope 2 which the bronchoscope navigation device 6 performs in order to help insert the bronchoscope 2 for observation or treatment after a route is determined as mentioned above. Incidentally, the description will be made by taking for instance a case where the number of branch points on a route is ten.

As described in FIG. 11, when the bronchoscope navigation device 6 starts navigation, a navigation screen 51 like the one shown in FIG. 12 is displayed on the monitor 5 at step S21.

The navigation screen 51 comprises: an endoscopic live image display area 52 in which a live image captured by the bronchoscope 2 is displayed; a VBS image display area 53 in which a VBS image is displayed; and a thumbnail VBS image area 54 in which images formed reducing VBS images representing branch points on a route are displayed as branch thumbnail VBS images. At step S21 at which the bronchoscope 2 has not yet been inserted, no live image is displayed in the endoscopic live image display area 52. However, a VBS image 53a depicting the first branch point on the route is displayed in the VBS image display area 53. Thumbnail VBS images 54(a) to 54(j) representing all the branch points are displayed in the thumbnail VBS image area 54.

A marker 55 is superimposed on the VBS image 53a in order to indicate a lumen of a path that advances along the route. Moreover, the frame of the thumbnail VBS image representing the same branch point as the VBS image 53a displayed in the VBS image display area 53 is displayed in boldface or in color so that the thumbnail VBS image can be discriminated from the others. An operator can easily discern which of the branch points is represented by a VBS image displayed in the VBS image display area 53. In the stage of step S21, the frame of the thumbnail VBS image 54(a) is displayed in boldface or in color.

At step S22, inserting the bronchoscope 2 into bronchi is started. As shown in FIG. 13, at step S23, a live image 52a captured by the bronchoscope 2 is displayed in the endoscopic live image display area 52 within the navigation screen 51. Even in FIG. 13, the VBS image 53a representing the first branch point on the route is displayed in the VBS image display area 53, and the thumbnail VBS images 52(a) to 54(j) representing all the branch points are displayed in the thumbnail VBS image area 54. The frame of the thumbnail VBS image 54(a) is displayed in boldface or in color.

Next, it is judged at step S24 whether navigation mode is set to mode 1 in the image processing unit 17 that has received a live image.

To begin with, navigation to be performed by the bronchoscope navigation device 6 will be described on the assumption that the navigation mode is set to mode 1.

First, when the distal end of the bronchoscope 2 reaches a first branch point, an operator judges whether or not to press the Freeze switch SW4. If the operator can discern the image of the lumen of the path indicated with the marker 55 on the live image 52a *by merely viewing the VBS image 53a* in the VBS image display area 53 and the live image 52a, the operator keeps inserting the bronchoscope. If it is hard to discern the lumen of the path indicated with the marker 55 on the live image 52a, the operator presses the Freeze switch SW4.

At step S25, it is judged whether the Freeze switch SW4 is turned on. If the Freeze switch SW4 is turned on, a still image acquired from the live image 52a is fetched at step S26. The still image and the VBS image 53a representing the first branch point are compared with each other in order to detect the degree of similarity between them according to a known image processing technique. If the Freeze switch SW4 is not turned on, control is passed to step S27.

If it is found at step S26 that the degree of similarity is equal to or smaller than a predetermined value, it is judged that the bronchoscope has been inserted along a route other than the determined route (or, the still image is compared with a VBS image representing a different branch point). Consequently, a warning is displayed (not shown).

If it is judged at step S26 that the still image of the live image 52a and the VBS image 53a resemble each other at a degree of similarity exceeding the predetermined value, both the images are regarded to represent the same branch point.

The operator then handles the Auto Image Rotation switch SW2 or Manual Image Rotation switch SW3 so as to rotate the VBS image 53a so that the still image of the live image 52a and the VBS image 53a will be matched with each other. Thereafter, control is passed to step S27.

Incidentally, when an operator presses the Auto Image Rotation switch SW2, the still image of the live image 52a and the VBS image 53a are automatically matched with each other through, for example, pattern recognition processing. Moreover, when the operator presses the Manual Image Rotation switch SW3, the VBS image 53a is rotated by a predetermined angle. The operator repeatedly presses the switch SW3 so as to match the live image 52a and VBS image 53a with each other.

After the still image of the live image 52a and the VBS image 53a are thus matched with each other, the operator can now discern the lumen of the path that is indicated with the marker 55 on the live image 52a. The operator therefore keeps inserting the bronchoscope according to the directive by the marker 55.

At step S27, it is judged whether the operator has pressed the Next VBR switch SW1. If the Next VBR switch SW1 is not pressed, control is returned to step S25. If the operator has pressed the Next VBR switch SW1, the VBS image 53a corresponding to a thumbnail VBS image (b) representing the next (second) branch point is displayed in the VBS image display area 53. At this time, the frame of the thumbnail VBS image 54(b) representing the second branch point is displayed in boldface or in color. The frame of the thumbnail VBS image 54(a) becomes the same as the frames of the other thumbnail VBS images.

At step S29, it is judged whether the bronchoscope has reached a lesion (that is, reached the end point of navigation). If the bronchoscope has reached the lesion, the process is terminated. If the bronchoscope has not reached the lesion, control is returned to step S25. The process from step S25 to step S29 is repeated until the bronchoscope reaches the lesion.

A concrete example of the process from step S25 to step S29 will be described in conjunction with the navigation screen 51. As shown in FIG. 14, assuming that the bronchoscope has been navigated to reach the eighth branch point, the VBS image 53a corresponding to a thumbnail VBS image 54(h) representing the eighth branch point is displayed in the VBS image display area 53. The live image 52a representing a region near the eighth branch point is displayed in the endoscopic live image display area 52. At this time, only the frame of the thumbnail VBS image 54(h) representing the eighth branch point is displayed in boldface or in color. This allows an operator to recognize that navigation is performed at the eighth branch point.

In this state, if the operator presses the Freeze switch SW4 (step S25), a still image acquired from the live image is fetched. If the operator presses the Auto Image Rotation switch SW2, the VBS image 53a is rotated as shown in FIG. 15 so that the still image of the live image 52 and the VBS image 53a will be matched with each other (step S26).

Thereafter, after the operator recognizes the lumen of the path that is a destination of insertion, if the operator presses the Next VBS switch SW1 (step S27), the VBS image 53a corresponding to a thumbnail VBS image 54(i) representing the ninth branch point is displayed in the VBS image display area 53. Only the frame of the thumbnail VBS image 54(i) representing the ninth branch point is displayed in boldface or in color, whereby the operator recognizes that the next position of navigation is the ninth branch point (step S28). Navigation is repeated in the same manner until the bronchoscope reaches the lesion (that is, the end point of navigation) (step S29).

Next, a description will be made of navigation to be performed by the bronchoscope navigation device 6 in a case where the navigation mode is set to mode 2.

If it is judged at step S24 described in FIG. 11 that the navigation mode is not set to mode 1 in the image processing unit 17 having received a live image but set to mode 2, control is passed to step S41 in FIG. 17.

The navigation mode 2 is mode to be utilized by an operator who has the expertise in inserting a bronchoscope into bronchi. When an operator expects navigation but has a thorough knowledge of lumens of paths that are destinations inserted at almost all branch points, the operator designates the mode 2 instead of the mode 1 because he/she does not need the navigation to a predetermined position at each branch point.

However, in mode 1, every time the bronchoscope reaches a branch point, the Next VBS switch SW1 is pressed. The position of a branch point represented by a live image can therefore be matched with the position thereof represented by a VBS image. However, assume that navigation is not needed at each branch point until a bronchoscope reaches a predetermined position, insertion is continued, and navigation is expected at a certain branch point. In this case, it is hard to find a thumbnail VBS image representing the branch point at which navigation is expected.

In the navigation mode 2, a thumbnail VBS image representing a branch point at which navigation is expected is searched based on a degree of insertion to which the insertion unit of a bronchoscope is inserted. The thumbnail VBS image 53a is then displayed in the VBS image display area 53, whereby navigation is enabled.

To be more specific, in navigation mode 2, if an operator does not need navigation, the operator continues insertion of the bronchoscope 2 while monitoring a live image. When the distal end of the bronchoscope 2 reaches a branch point at which the operator needs navigation, the operator presses the Freeze switch SW4.

Navigation to be performed by the bronchoscope navigation device 6 in mode 2 is described in FIG. 17. Namely, at step S41, it is waited until the Freeze switch SW4 is pressed. If the switch SW4 is pressed, a reduced image 60 of a still image acquired with the press of the Freeze switch SW4 is superimposed on the live image 52a displayed in the endoscopic live image display area 52.

Referring to FIG. 18, when the Freeze switch SW4 is pressed, the bronchoscope lies at the eighth branch point. Navigation has not been needed by this time. The Freeze switch SW4 is pressed for the first time. The VBS image 53a displayed in the VBS image display area 53 is a VBS image corresponding to a thumbnail VBS image 54(a) representing the first branch point.

At step S43, the degree-of-insertion detection unit 3 detects a degree of insertion to which the insertion unit of the bronchoscope 2 has been inserted into a patient body. At step S44, the position of the distal end of the bronchoscope 2 and the position of a nearby branch point are calculated based on the detected degree of insertion.

At step S45, VBS images representing regions started with a branch point immediately preceding the calculated branch point and ended with an immediately succeeding branch point are displayed in the form of a motion picture in the VBS image display area 53. Moreover, the frame of only a thumbnail VBS image representing the calculated branch point is displayed in boldface or in color.

FIG. 19 shows display of a motion picture composed of VBS images representing regions that start with the seventh branch point immediately preceding the eighth branch point, which is shown in FIG. 18 and serves as a reference point, and that end with the ninth branch point immediately succeeding the eighth branch point. FIG. 20 shows the navigation screen 51 with the VBS image 53a being displayed, which represents the seventh branch point and with which display of the motion picture is started, displayed in the VBS image display area 53 thereof. FIG. 21 shows the navigation screen 51 with the VBS image 53a being displayed, which represents the ninth branch point and with which the display of the motion picture is terminated, displayed in the VBS image display area 53 thereof.

As shown in FIG. 20 and FIG. 21, a motion picture domain bar 71 that indicates a domain to be displayed in the form of a motion picture in the VBS image display area 53 is displayed below the thumbnail VBS images displayed in the thumbnail VBS image area 54. FIG. 20 and FIG. 21 show examples of display in which the motion picture domain bar 71 is displayed below the thumbnail VBS images that start with the thumbnail VBS image 54(g) representing the seventh branch point and that end with the thumbnail VBS image 54(i) representing the ninth branch point. At this time, the frame of only the thumbnail VBS image 54(h) representing the calculated branch point is displayed in boldface or in color.

Consequently, an operator can recognize at what branch point the distal end of the insertion unit is currently located. The operator can therefore advance or withdraw the inserted bronchoscope so as to find out a live image representing a nearby branch point. Eventually, the live image 52a representing the branch point is displayed in the endoscopic live image display area 52.

Once the live image 52a representing a position at which navigation is needed is thus displayed, it is waited at step S46 until the Freeze switch SW4 is turned on. If the switch SW4 is turned on, a still image of the live image 52a is fetched at step S47. The VBS image 53a representing the calculated branch point is displayed in the VBS image display area 53. At step S48, the still image of the live image 52a and the VBS image 53a representing the calculated branch point are compared with each other in order to detect the degree of similarity between the images according to the known image processing technique. A process similar to the one executed in mode 1 is then executed.

In the state shown in FIG. 21, if the Freeze switch SW4 is turned on, the VBS image 53a corresponding to the thumbnail VBS image 54(h) representing the calculated branch point is, as shown in FIG. 22, displayed in the VBS image display area 53. Moreover, the frame of only the thumbnail VBS image 54(h) representing the calculated branch point is displayed in boldface or in color.

At step S48, similarly to the one in mode 1, if the degree of similarity is equal to or smaller than a predetermined value, it is judged that the bronchoscope has been inserted along a route other than a determined route (or the still image is compared with a VBS image representing a different branch point). A warning is then displayed (not shown).

Moreover, at step S48, similarly to the one in mode 1, if it is judged that the degree of similarity exceeds the predetermined value and the still image of the live image 52a and the VBS image 53a resemble each other, both the images are regarded to represent the same branch point. An operator then handles the Auto Image Rotation switch SW2 or Manual Image Rotation switch SW3 so as to rotate the VBS image 53a. The still image of the live image 52a and the VBS image 53a are thus matched with each other. Thereafter, control is passed to step S49.

Once the still image of the live image 52a and the VBS image 53a are matched with each other, an operator can easily discern a lumen of a path that is indicated with the marker 55 on the live image 52a. The operator continues insertion according to the directive given with the marker 55.

At step S49, it is judged whether the bronchoscope has reached a lesion (that is, whether the bronchoscope has reached the end point of navigation). If the bronchoscope has reached the lesion, the process is terminated. If the bronchoscope has not reached the lesion, control is returned to step S41. The process from step S41 to step S49 will be repeated until the bronchoscope reaches the lesion.

At step S45, VBS images representing regions that start with a branch point immediately preceding a calculated branch point serving as a reference point and that end with an immediately succeeding branch point are displayed in the form of a motion picture in the VBS image display area 53. The present invention is not limited to this mode. Alternatively, VBS images representing regions that start with a branch point of two points preceding a calculated branch point serving as a reference point and that end with a two point succeeding branch point may be displayed in the form of a motion picture in the VBS image display area 53.

According to the present embodiment, when navigation is performed in mode 1, thumbnail VBS images representing all branch points are displayed in the thumbnail VBS image area 54. Moreover, the frame of a thumbnail VBS image corresponding to the VBS image 53a, which is compared with the live image 52a, is displayed in boldface or in color. Consequently, which of branch points is represented by the live image 52a can be easily discerned.

Moreover, when navigation is performed in mode 2, the VBS image 53a representing a branch point at which navigation is needed can be retrieved easily. The VBS images 53a representing regions near a region represented by the live image 52a are displayed in the form of a motion picture. Consequently, what branch point is represented by the live image 52a can be easily discerned.

Furthermore, when navigation is performed in mode 1 or 2, the live image 52a and VBS image 53a are compared with each other, and the degree of similarity between the images is calculated according to an image processing technique. If the degree of similarity is equal to or smaller than a predetermined value, a warning is given. An operator suspends insertion at a branch point which the operator has misidentified. The operator can easily dispose the distal end of the bronchoscope 2 at an appropriate branch point.

Incidentally, in the navigation screen 51, the frame of the thumbnail VBS image that corresponds to the VBS image 53a and that is displayed in the thumbnail VBS image area 54 is displayed in boldface or in color. As shown in FIG. 23, the thumbnail VBS image corresponding to the VBS image 53a may be enlarged, and the frame of the enlarged thumbnail VBS image may be displayed in boldface or in color. Referring to FIG. 23, the number of branch points is nine, and the VBS image 53a corresponding to the thumbnail VBS image representing the seventh branch point is displayed.

In the navigation screen 51, thumbnail VBS images representing branch points are displayed in a row. If the number of branch points is large, thumbnail VBS images representing branch points may be, as shown in FIG. 24, displayed in two or more rows. Moreover, as shown in FIG. 25, if the frame of the thumbnail VBS image area 54 is structured such that thumbnail VBS images can be scrolled, a plurality of thumbnail VBS images can be scrolled and thus displayed.

Furthermore, the marker 55 is superimposed on the VBS image 53a in the navigation screen 51 in order to indicate a lumen of a path extending along a route. The present invention is not limited to this mode. For example, as shown in FIG. 26, the contour of the periphery of a lumen of a path extending along a route which is depicted in the VBS image 53a may be displayed while being enhanced. Otherwise, the interior of a lumen of a path may be depicted in color.

Furthermore, as shown in FIG. 27, upward and downward directions (directions of gravity) depending on a patient's posture may be indicated in the VBS image 53a within the navigation screen 51. The upward and downward directions may also be, as shown in FIG. 28, indicated in the live image 52a.

Moreover, as shown in FIG. 29, a marker 81 may be superimposed on the VBS image 53a in order to indicate the position of a tissue that is an object of biopsy and that is located at a destination of insertion. The distance from a current position to the position of the tissue that is an object of biopsy and the diameter of the tissue may be indicated in the VBS image 53a. Instead of the marker 81, a tissue image 82 that is patterned after the diameter or shape of a tissue may be displayed on the VBS image 53a.

Therefore, according to the present embodiment, an endoscope can be reliably navigated to reach a target region using guide images representing actual branch positions.

The present invention is not limited to the foregoing embodiment. Various modifications and variations can be made within the gist of the present invention.

INDUSTRIAL APPLICABILITY

As mentioned above, an endoscope device in accordance with the present invention will prove effective when used as: an endoscope device that navigates an endoscope so as to help insert the endoscope into an intracorporeal lumen; an endoscope device that navigates a bronchoscope so as to help insert the bronchoscope into an intracorporeal lumen such as bronchi; or an endoscope device for industrial use that navigates an endoscope so as to help insert the endoscope into a lumen that branches out at points in multiple stages. In particular, when a target region is located at a terminal of an intracorporeal lumen that branches out at points in multiple stages, such as, bronchi, an endoscope device in accordance with the present invention is the most suitable for reliably navigating the distal end of a bronchoscope.

The invention claimed is:

1. An endoscope device comprising:
   three-dimensional image constructing means for constructing a three-dimensional image of an intracorporeal lumen of a subject on the basis of image data acquired from a three-dimensional field of the subject;
   an endoscope for imaging the intracorporeal lumen of the subject;
   a degree-of-insertion calculating means for calculating a degree-of-insertion to which the endoscope is inserted;
   a route determination means that determines a route, which starts with a point at which the endoscope is inserted and ends with a point at which the endoscope reaches a target region of the subject based upon physical structure depicted in the three-dimensional image and that links the start and end points, so that the course of the endoscope to be steered in order to insert the endoscope can be presented;
   and
   navigation image constructing means for constructing a navigation image, which includes an endoscopic image that is produced by the endoscope and that represents the intracorporeal lumen of the subject, a plurality of reduced thumbnail images, each of the plurality of reduced thumbnail images is of the three-dimensional image constructed by the three-dimensional image constructing means and representing a branch point at which the intracorporeal lumen of the subject branches out, the plurality of reduced thumbnail images are displayed in series in an order from a point at which the endoscope is inserted to a point at which the endoscope reach a target region of the subject and the three-dimensional image, said three-dimensional image is adapted for being rotatably displayed, so that while presenting the course of the endoscope to be steered in order to insert the endoscope into the intracorporeal lumen of the subject, the endoscope device can help observe or treat the interior of the subject, wherein:
   the navigation image constructing means displays the plurality of reduced thumbnail images in a manner that allows identification of which of the plurality of reduced thumbnail images corresponds to a branch point near a distal section of the endoscope based on the degree-of-insertion calculated by the degree-of-insertion calculating means, and which rotates and displays the three-dimensional image so that the endoscopic image and the three-dimensional image are matched with each other if a degree of similarity in images between a still image of the endoscopic image and the three-dimensional image corresponding to the identifiably displayed reduced thumbnail image is equal to or larger than a predetermined threshold value.

2. The endoscope device according to claim 1, wherein the navigation image constructing means comprises: an image processing unit that constructs the plurality of reduced thumbnail images, each of said plurality of reduced thumbnail images is a three-dimensional image representing a branch point on the determined route, according to the result of determination performed by the route determination means, wherein the image processing units added the constructed plurality of reduced thumbnail images to the navigation image.

3. The endoscopic imaging system according to claim 2, further comprising image display control means that displays the navigation image, which is constructed by the image processing unit included in the navigation image constructing means, on a monitor.

4. The endoscope device according to claim 3, further comprising operational input means for use in giving an operational directive to the route determination means and image display control means.

5. The endoscope device according to claim 3, wherein the image display control means rotates the three-dimensional image contained in the navigation image displayed on a monitor, and displays it.

6. The endoscope device according to claim 2, wherein the route determination means determines a plurality of routes that starts with the point at which the endoscope is inserted and ends with the point at which the endoscope reaches the target region.

7. The endoscope device according to claim 2, wherein the route determination means displays a determined route by superimposing the determined route through a display screen image of the three-dimensional image that represents the intracorporeal lumen of the subject and that is constructed by the three-dimensional image constructing means.

8. The endoscope device according to claim 2, wherein: the navigation image constructing means includes multi-screen reconstructed image constructing means that constructs a multi-screen reconstructed image, which represents the intracorporeal lumen of the subject, on the basis of the image data acquired from the three-dimensional field of the subject; and the route determination means determines the route through a display screen image of the multi-screen reconstructed image constructed by the multi-screen reconstructed image constructing means.

9. The endoscope device according to claim 8, wherein: the three-dimensional image is a virtual endoscopic image that represents the intracorporeal lumen of the subject and that is constructed based on CT image data which is the image data acquired from the three-dimensional field of the subject; and the multi-screen reconstructed image represents the intracorporeal lumen of the subject and that is constructed based on the CT image data.

10. The endoscope device according to claim 9, wherein the image processing unit constructs plurality of reduced thumbnail images using the multi-screen reconstructed image, which is constructed by the multi-screen reconstructed image constructing means, according to the result of calculation performed by the route determination means.

11. The endoscope device according to claim 9, wherein the three-dimensional image constructing means constructs a succession of the virtual endoscopic images, which represent regions along the route determined by the route determination means, in units of a frame in synchronization with the endoscopic image.

12. The endoscope device according to claim 9, further comprising: a fetching unit that fetches the CT image data; a first storage unit in which the CT image data fetched by the fetching unit is stored; and a second storage unit in which image data representing the virtual endoscopic images is stored.

13. An endoscope device, comprising:
three-dimensional image constructing means for constructing a three-dimensional image of an intracorporeal lumen of a subject on the basis of image data acquired from a three-dimensional field of the subject;
an endoscope that images the intracorporeal lumen of the subject;
a degree-of-insertion calculating means for calculating a degree-of-insertion to which the endoscope is inserted;
first navigation image constructing means for constructing a navigation image that includes an endoscopic image, which is produced by the endoscope and represents the intracorporeal lumen of the subject, and the three-dimensional image, which is rotated and displayed so that the endoscopic image and the three-dimensional image are matched with each other based if a degree of similarity in images between a still image of the endoscopic image and the three-dimensional image is equal to or larger than a predetermined threshold value;
route determining means for determining a route that starts with a point at which the endoscope is inserted and ends with a point at which the endoscope reaches a target region of the subject based upon physical structure depicted in the three-dimensional image and that links the start and end points, and that is used to present the course of the endoscope to be steered in order to insert the endoscope;
second navigation image constructing means for constructing a plurality of reduced thumbnail images, each of said plurality of reduced thumbnail images is of the three-dimensional image constructed by the three-dimensional image constructing means and representing a branch point on the determined route at which the lumen branches out, according to the result of calculation performed by the route determining means, and displaying the plurality of reduced thumbnail images on the navigation image in series in an order of the determined route from the start point to the end point in a manner allowing the identification of which one of said plurality of reduced thumbnail images corresponds to the displayed three-dimensional image where said three-dimensional image is an image of a branch point near a distal section of the endoscope, based upon the degree-to-insertion calculated by the degree-of-insertion calculating means; and
image display control means for displaying the navigation image, which is constructed by the second navigation image constructing means, on a monitor.

14. A navigation method implemented in an endoscope device, comprising:
a three-dimensional image constructing procedure for constructing a three-dimensional image of an intracorporeal lumen of a subject on the basis of image data acquired from a three-dimensional field of the subject;
a degree-of-insertion calculating procedure for calculating a degree-of insertion to which the endoscope device is inserted;
a first navigation image constructing procedure for constructing a navigation image that includes an endoscopic image, which represents the intracorporeal lumen of the subject and is produced by an endoscope that picks up images of an intracorporeal lumen of a subject, and the three-dimensional image, which is rotated and displayed so that the endoscopic image and the three-dimensional image are matched with each other based if a degree of similarity in images between a still image of the endoscopic image and the three-dimensional image is equal to or larger than a predetermined threshold value;
a route determining procedure for determining a route that starts with a point at which the endoscope is inserted and ends with a point at which the endoscope reaches a target region of the subject based upon physical structure depicted in the three-dimensional image and that links the start and end points, and that is used to present the course of the endoscope to be steered in order to insert the endoscope;
a second navigation image constructing procedure for constructing a plurality of reduced thumbnail images, each of said plurality of reduced thumbnail images is of the three-dimensional image constructed by the three-dimensional image constructing means and representing a branch point on the determined route at which the lumen branches out, according to the result of calculation performed according to the route determining procedure, and displaying the plurality of reduced thumbnail images on the navigation image in series in an order of the determined route from the start point to the end point in a manner allowing the identification of which one of said plurality of reduced thumbnail images corresponds to the displayed three-dimensional image, where said three-dimensional image is an image of a branch point near a distal section of the endoscope, based upon the degree-to-insertion;

an image display control procedure for displaying the navigation image, which is constructed according to the second navigation image constructing procedure, on a monitor.

15. The navigation method implemented in an endoscope device according to claim 14, wherein the rotation comprising:

generating a still image from the endoscopic image;

determining a degree of similarity of the still image of the endoscopic image and the three-dimensional image; and rotating the three-dimensional image based upon the determining.

16. The navigation method implemented in an endo scope device according to claim 15, wherein the rotating of the three-dimensional image is automatically performed.

* * * * *